US010626120B2

(12) United States Patent
Roberge et al.

(10) Patent No.: US 10,626,120 B2
(45) Date of Patent: Apr. 21, 2020

(54) N-DEMETHYLATION OF MORPHINAN ALKALOIDS

(71) Applicant: Noramco, LLC, Wilmington, DE (US)

(72) Inventors: Dominique Roberge, Sierre (CH); Petteri Elsner, Brig (CH); Christian Oliver Kappe, Graz (AT); Bernhard Gutmann, Graz (AT); Ulrich Weigl, Hilzingen (DE); Douglas Phillip Cox, Eagleville, PA (US)

(73) Assignee: Noramco, LLC, Wilmington, DE (US)

( * ) Notice: Subject to any disclaimer, the term of this patent is extended or adjusted under 35 U.S.C. 154(b) by 0 days.

(21) Appl. No.: 16/095,604

(22) PCT Filed: Apr. 21, 2017

(86) PCT No.: PCT/US2017/028838
§ 371 (c)(1),
(2) Date: Oct. 22, 2018

(87) PCT Pub. No.: WO2017/184979
PCT Pub. Date: Oct. 26, 2017

(65) Prior Publication Data
US 2019/0330221 A1 Oct. 31, 2019

Related U.S. Application Data

(60) Provisional application No. 62/326,087, filed on Apr. 22, 2016.

(51) Int. Cl.
*C07D 491/08* (2006.01)
*B01J 23/44* (2006.01)

(52) U.S. Cl.
CPC ............ *C07D 491/08* (2013.01); *B01J 23/44* (2013.01)

(58) Field of Classification Search
None
See application file for complete search history.

(56) References Cited

U.S. PATENT DOCUMENTS

| 4,264,776 | A | 4/1981 | Hershman et al. |
| 8,946,214 | B2 | 2/2015 | Hudlicky et al. |
| 8,957,072 | B2 | 2/2015 | Hudlicky et al. |
| 2006/0189166 | A1 | 8/2006 | Tesfu et al. |
| 2009/0005564 | A1 | 1/2009 | Carroll et al. |
| 2009/0005565 | A1 | 1/2009 | Carroll et al. |
| 2009/0156815 | A1 | 6/2009 | Wang et al. |
| 2011/0306766 | A1 | 12/2011 | Bos et al. |
| 2011/0313163 | A1 | 12/2011 | Hudlicky et al. |
| 2012/0226043 | A1 | 9/2012 | Scammella et al. |
| 2012/0283443 | A1 | 11/2012 | Hudlicky et al. |

FOREIGN PATENT DOCUMENTS

WO WO-2005/002848 A1 1/2005

OTHER PUBLICATIONS

International Search Report and Written Opinion for PCT Application No. PCT/US2017/028894, dated Aug. 29, 2017, 9 pages.
International Search Report and Written Opinion for corresponding PCT Application No. PCT/US2017/028838, dated Aug. 1, 2017, 7 pages.
Machara et al, "Direct Synthesis of Naltrexone by Palladium-Catalyzed N-Demethylation/Acylation of Oxymorphone. The Benefit of C-H Activation and the Intramolecular Acyl Transfer from C-14 I Hydroxyl", Advanced Synthesis & Catalysis, (2012), vol. 354 (14-15), 25 pages.
Machara, A., et al., Improved Synthesis of Buprenorphine from Thebaine and/or Oripavine via Palladium-Catalyzed N-Demethylation/Acylation and/or Concomitant O-Demethylation: Advanced Synthesis & Catalysis (2012), vol. 354 (4) pp. 613-626.
Werner, L., et al., "Unexpected N-Demethylation of Oxymorphone and Oxycodone M-Oxides Mediated by the Burgess Reagent: Direct Synthesis of Naltrexone, Naloxone, and Other Antagonist from Oxymorphone", Advanced Synthesis & Catalysis, (2012), pp. 2706-2712, vol. 354(14-15).
Carroll, R.J. et al., "Palladium-Catalyzed N-Demethylation/N-Acylation of Some Morphine and Tropane Alkaloids" Advanced Synthesis & Catalysis, (2008), vol. 350, pp. 2984-2992.
Hosztafi, S. et al. "Synthesis of New Morphine Derivatives Containing Halogen of the Aromatic Ring" Synthetic Communications, (1994), 24, pp. 3031-3045.
Ninan, A. et al., "An improved synthesis of noroxymorphone", Tetrahedron, (1992), vol. 48, pp. 6709-6716.
Gutmann, B. et al., "Towards the Synthesis of Noroxymorphone via Aerobic Palladium-Catalyzed Continuous Flow N-Demethylation Strategies" ACS Sustainable Chem. Eng., (Jul. 22, 2016), 4, DOI: 10.1021/acssuschemeng.6b01371; 35 pages.
Gutmann, B. et al., "Batch-and Continuous-Flow Aerobic Oxidation of 14-Hydroxy Opioids to 1,3-Oxazolidines-A Concise Synthesis of Noroxymorphone" Chemistry A European Journal, (2016), 22, pp. 1-7.
Dong, Z. et al., "New Methodology for the N-Demethylation of Opiate Alkaloids" JOC Article, (2007), 72, pp. 9881-9885.
Kok, G. et al., "An Improved Process for the N-Demethylation of Opiate Alkaloids using an Iron (II) Catalyst in Acetate Buffer" Advanced Synthesis & Catalysis, (2009), 351, pp. 283-286.

*Primary Examiner* — Zinna Northington Davis
(74) *Attorney, Agent, or Firm* — Alston & Bird LLP

(57) ABSTRACT

The present disclosure relates to N-demethylation of a compound containing a tertiary N-methylamine, including for example a morphinan alkaloid, in a continuous flow system. In particular, the present disclosure relates to N-demethylation of oxymorphone-3,14-diacetate or 14-hydroxymorphinone-3,14-diacetate using highly active catalytic palladium (0) in a continuous flow system under elevated temperature and pressure condition. The methodology can be utilized towards the synthesis of noroxymorphone via aerobic palladium-catalyzed continuous flow N-demethylation.

24 Claims, 7 Drawing Sheets

Pd(0) Catalyzed Oxidative N-Demethylation.

Pd(OAc)$_2$-Catalyzed Aerobic N-Demethylation/Dehydrogenation of Oxymorphone 3,14-Diacetate (1).

Pd(OAc)$_2$-Catalyzed Aerobic N-Demethylation/Dehydrogenation of Hydroxymorphinone 3,14-Diacetate (2).

Pd(OAc)$_2$-Catalyzed Aerobic N-Demethylation of 14-Hydroxymorphinone 3,14-Diacetate (3).

N-DEMETHYLATION OF MORPHINAN ALKALOIDS

CROSS-REFERENCE TO RELATED APPLICATIONS

This application is a U.S. National Stage of International Patent Application No. PCT/US2017/028838, filed Apr. 21, 2017, which claims the benefit of U.S. Provisional Application No. 62/326,087, filed Apr. 22, 2016 each of which is incorporated herein by reference in its entirety.

FIELD OF THE TECHNOLOGY

The present disclosure relates to N-demethylation of a morphinan alkaloid compound containing a tertiary N-methylamine in a continuous flow system. In particular, the present disclosure relates to the synthesis of a morphinan alkaloid compound, and related compounds, via aerobic catalyzed continuous flow N-demethylation.

BACKGROUND OF THE INVENTION

Many naturally occurring alkaloids, including tropane alkaloids (e.g., atropine, scopolamine, cocaine) and morphinan alkaloids (e.g., morphine, codeine, oripavine, thebaine) contain a tertiary N-methylamine group (See FIG. 1). Modification of this N-methylamine group can have a profound effect on the pharmacological properties of the modified molecule. The synthesis of a wide range of clinically relevant molecules include replacing the N-methyl group with different alkyl groups. For example, the replacement of the N-methyl group for an N-allyl or an N-cyclopropylmethyl group N-demethylation/N-alkylation generates the potent opioid receptor antagonists naloxone and naltrexone. Naloxone is a potent pure opioid antagonist and is a first line treatment for patients experiencing an opioid overdose. In many countries it is necessitated to be in place whenever opioids are administered to reverse the effects of the narcotic agonists. Naltrexone, on the other hand, is primarily used for the management of opioid and alcohol dependence. N-Demethylation is also a significant step in the synthesis of mixed opioid agonist-antagonists such as nalorphine, nalbuphine and buprenorphine (See FIG. 1). The replacement of the N-methyl group with longer N-alkyl groups can provide or restore agonist activity. For example, N-phenethylnormorphine has a 10-fold greater potency than morphine itself.

A number of methods for the N-demethylation of tertiary amines are known. Some methods for the removal of the N-methyl group involve the use of reagents such as cyanogen bromide or chloroformates. The reactions involved with these methods produce cyanamides and carbamates, respectively, which can be readily hydrolyzed to the corresponding amines. Similar transformations can be achieved with diethyl azodicarboxylate or N-iodosuccinimide. These methods, however, use highly toxic and corrosive reagents in stoichiometric amounts and also generate stoichiometric amounts of waste products. N-Demethylation can also be achieved using N-oxides, but such use requires multiple steps. N-Demethylation using N-oxides is typically performed by oxidation of the alkaloid to the corresponding N-oxide, isolation of the N-oxide as the hydrochloride salt, and subsequent activation and decomposition of the N-oxide to the N-demethylated product.

Laboratory scale processes for the catalytic oxidative N-demethylation of morphine-type alkaloids in the presence of an oxidant, such as oxygen gas, are known. The practical application of these processes on a commercial scale is limited, in part, due to the fact that conventional batch reactors are poorly suited to address the distinct process challenges and safety risks associated with reactions with molecular oxygen. For example, gas-liquid reactions can be dominated by mass transfer effects and even short periods of poor gas-liquid mixing can adversely affect reaction kinetics and selectivity, or lead to irreversible decomposition of a catalyst. Furthermore, reactions with oxygen gas can be highly exothermic or result in fires or explosions in the presence of flammable solvents.

The present disclosure addresses these concerns by using a continuous process having high mass and heat transport capabilities and suitable for multi-phase and highly exothermic reactions. Gaseous reagents can be easily and accurately added and mixed into the liquid phase using flow-based systems. Importantly, combustion and explosion hazards are reduced because gaseous reagents can be dissolved in flammable organic solvents at high pressure, minimizing or eliminating the possibility of a head space and therefore the possibility of fire or explosion. Consequently, reactions can be performed under unusually harsh process conditions in a safe and controllable manner (i.e. high temperature/high pressure conditions).

SUMMARY OF THE INVENTION

The present disclosure relates to N-demethylation of a morphinan alkaloid compound containing a tertiary N-methylamine in a continuous flow system. In particular, the present disclosure relates the synthesis of morphinan alkaloid compounds and related compounds via aerobic catalyzed (e.g., palladium) continuous flow N-demethylation. The present disclosure also relates to the scalable process for the preparation of noroxymorphone using a continuous flow system capable of catalyzed N-demethylation using molecular oxygen as the oxidant. The scalable process of the present disclosure can be utilized in an industrial process for the production of noroxymorphone by an N-demethylation-, hydrogenation-, and hydrolysis-reaction sequence.

In one embodiment, the present disclosure relates to a process for the N-demethylation of a compound containing a tertiary N-methylamine including the steps of providing a liquid mixture of the compound and a catalyst (e.g., metal catalyst such as palladium, platinum) in a solvent, contacting the liquid mixture with a gaseous oxidant or organic peroxide oxidant to form a reaction mixture, such that the compound and oxidant contained in the reaction mixture react to form a N-demethylated form of the compound in a continuous flow system, and optionally isolating the N-demethylated form of the compound.

The embodiments of the present disclosure address the disadvantages of the prior art, e.g., safety and reduction of waste by-products. The use of a continuous flow system reduces or eliminates the safety risks present in traditional batch synthesis, such as those based on the use of oxygen gas as an oxidant, including spontaneous ignition resulting in explosions. The small volumes, channel dimensions and/or reduced headspace of the continuous flow system can reduce explosion risks and allow a safe process for the N-demethylation of select compounds having an N-methylamine group and significantly reduces the amount of hazardous waste generated by the process.

BRIEF DESCRIPTION OF THE DRAWINGS

The foregoing and other advantages provided by the present disclosure will be more fully understood from the following description of exemplary embodiments when read together with the accompanying drawings, in which.

DETAILED DESCRIPTION OF THE INVENTION

Figure 1:
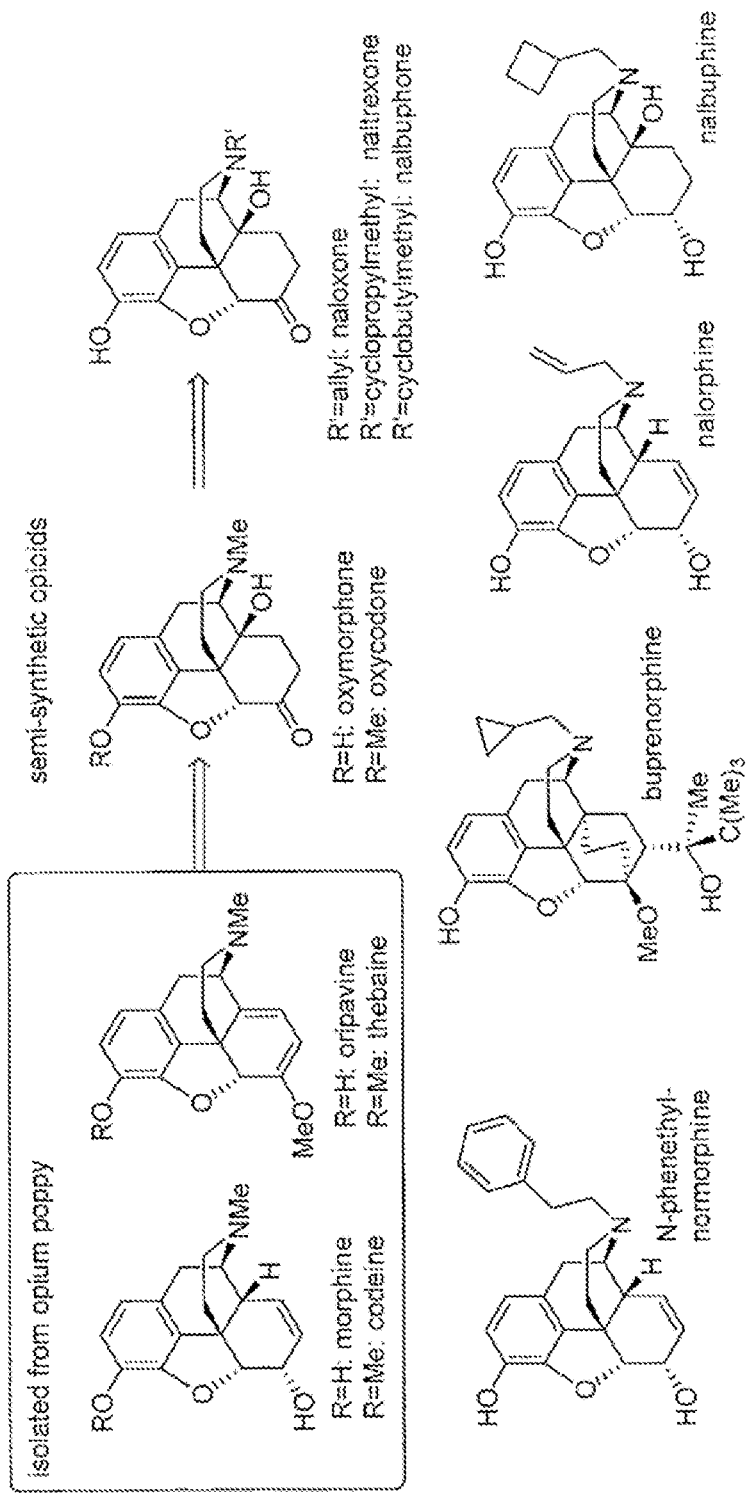
FIG. 1 shows exemplary naturally occurring morphine alkaloids and semi-synthetic derivatives.
Figure 2:
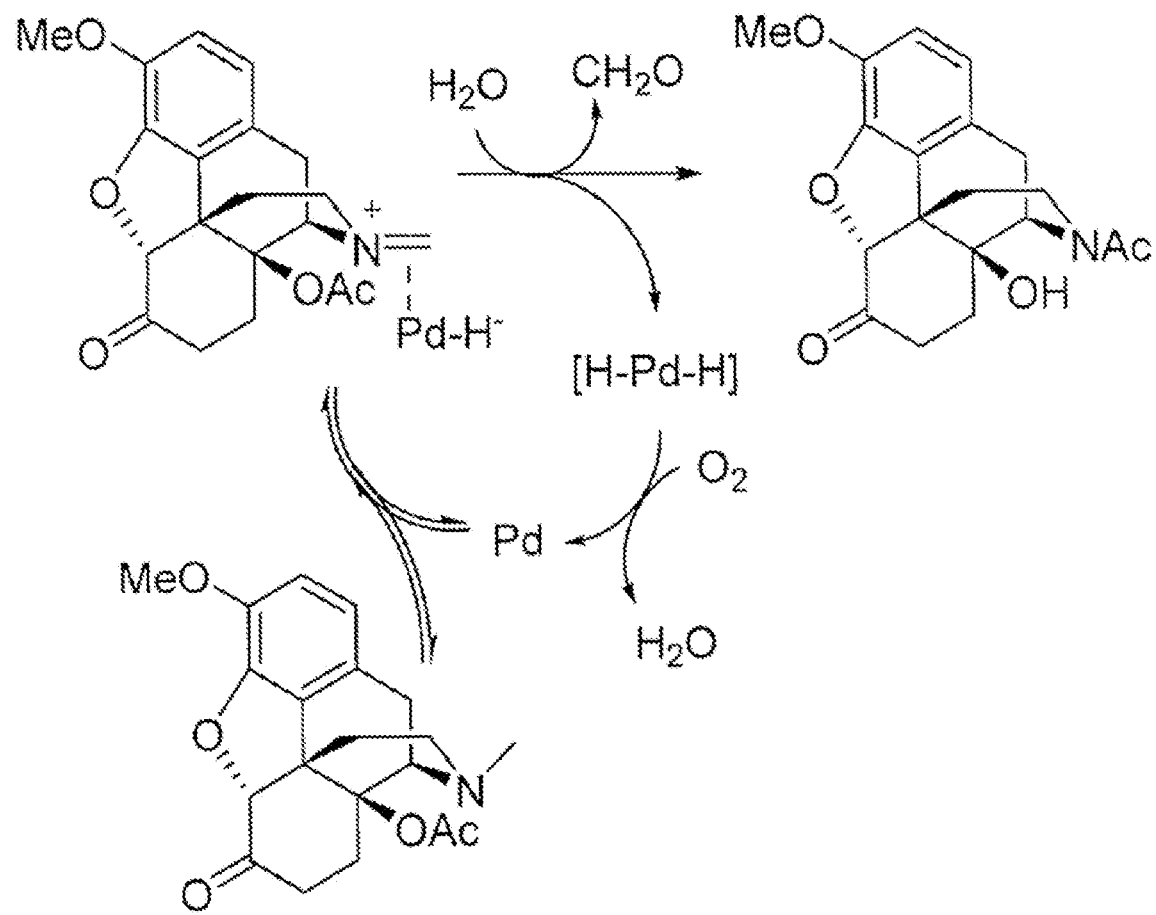
FIG. 2 shows an exemplary Pd(0) catalyzed oxidative N-demethylation.

The present disclosure relates to N-demethylation of a morphinan alkaloid compound containing a tertiary N-methylamine in a continuous flow system. In particular, the present disclosure relates the synthesis of morphinan alkaloid compounds and related compounds via aerobic catalyzed continuous flow N-demethylation. Aerobic N-demethylation using palladium(0) is shown in FIG. 2. The dealkylation of tertiary amines with palladium(0) under harsh conditions and in an inert atmosphere is known. The present disclosure relates to aerobic N-demethylation which can proceed under milder conditions and without the release of hydrogen.

In one embodiment, the present disclosure relates to a process for the N-demethylation of a compound containing a tertiary N-methylamine including the steps of providing a liquid mixture of the compound and a metal catalyst, e.g., a palladium or platinum catalyst, in a solvent, contacting the liquid mixture with a gaseous oxidant or organic peroxide oxidant to form a reaction mixture, whereby the compound and oxidant contained in the reaction mixture to form a N-demethylated form of the compound in a continuous flow system. The N-demethylated compound can thereafter be isolated.

The compound containing a tertiary N-methylamine can be any compound capable of undergoing N-demethylation in a continuous flow reactor system. For example, the compound can be a compound of the formula (I):

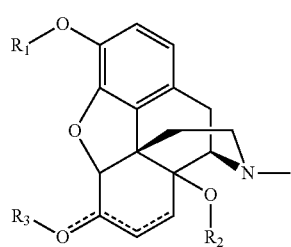

(I)

wherein each ===== independently represents a single or double bond, provided that two double bonds are not adjacent to each other;

$R_1$ and $R_3$ are each independently selected from the group consisting of C(O)$R_4$, $C_{1-10}$ alkyl, $C_{6-10}$ aryl, $C_{3-10}$ cycloalkyl, alkylene-$C_{6-10}$ aryl, $C_{1-10}$ alkylene-$C_{3-10}$ cycloalkyl and PG; and $R_2$ is selected from the group consisting of C(O)$R_4$, S(O)$R_4$, SO$_2R_4$, P(O)$R_4R_5$, P(O)(OR$_4$)$R_5$, and P(O)(OR$_4$)(OR$_5$);

$R_4$ and $R_5$ are each independently selected from $C_{3-10}$ cycloalkyl, $C_{3-10}$ heterocycloalkyl, $C_{3-10}$ cycloalkenyl, $C_{1-10}$ alkyl, $C_{2-10}$ alkenyl, $C_{6-10}$ aryl and $C_{5-10}$ heteroaryl, each of the latter groups being unsubstituted or substituted with one or more substituents independently selected from $C_{1-4}$ alkyl, $OC_{1-4}$ alkyl, halo, CN, NO$_2$, $C_{6-10}$ aryl and $OC_{6-10}$ aryl.

As used herein the term "alkyl" refers to, whether it is used alone or as part of another group, straight or branched chain, saturated alkyl groups. The term $C_{1-10}$ alkyl means an alkyl group having 1, 2, 3, 4, 5, 6, 7, 8, 9 or 10 carbon atoms. In some embodiments, one or more of the hydrogen atoms in the alkyl groups can be optionally replaced with a halogen.

As used herein the term "aryl" refers to cyclic groups that contain at least one aromatic ring. The aryl group can contain 6, 9 or 10 atoms, such as phenyl, naphthyl or indanyl. In some embodiments, one or more of the hydrogen atoms in the aryl groups can be optionally replaced with a halogen.

As used herein the term "cycloalkyl" refers to, whether it is used alone or as part of another group, cyclic, saturated alkyl groups. The term $C_{3-10}$ cycloalkyl means a cycloalkyl group having 3, 4, 5, 6, 7, 8, 9 or 10 carbon atoms. In some embodiments, one or more of the hydrogen atoms in the cycloalkyl groups can be optionally replaced with a halogen.

As used herein the term "alkylene" refers to, whether alone or as part of another group, an alkyl group that is bivalent; i.e. that is substituted on two ends with another group. The term $C_{1-10}$ alkylene means an alkylene group having 1, 2, 3, 4, 5, 6, 7, 8, 9 or 10 carbon atoms. In some embodiments, one or more of the hydrogen atoms in the alkylene groups can be optionally replaced with a halogen.

As used herein the term "PG" or protective group refers to a chemical moiety which protects or masks a reactive portion of a molecule to prevent side reactions in those reactive portions of the molecule, while manipulating or reacting a different portion of the molecule. After the manipulation or reaction is complete, the protecting group can be removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3rd Edition, 1999 and in Kocienski, P. Protecting Groups, 3rd Edition, 2003, Georg Thieme Verlag (The Americas). Examples of suitable protecting groups include, but are not limited to t-Boc, Ac, Ts, Ms, silyl ethers such as TMS, TBDMS, TBDPS, Tf, Ns, Bn, Fmoc, dimethoxytrityl, methoxyethoxymethyl ether, methoxymethyl ether, pivaloyl, p-methyoxybenzyl ether, tetrahydropyranyl, trityl, ethoxyethyl ethers, carbobenzyloxy, benzoyl and the like.

As used herein the term "heterocycloalkyl" refers to, whether it is used alone or as part of another group, cyclic, saturated alkyl groups containing at least one heteroatom, such as N, O, and/or S. The term $C_{3-10}$ heterocycloalkyl means a heterocycloalkyl group having 3, 4, 5, 6, 7, 8, 9 or 10 carbon atoms, in which at least one of the carbon atoms has been replaced with a heteroatom, such as N, O and/or S. In some embodiments, one or more of the hydrogen atoms in the heterocycloalkyl groups can be optionally replaced with a halogen.

As used herein the term "cycloalkenyl" refers to, whether it is used alone or as part of another group, cyclic, unsaturated alkyl groups. The term $C_{3-10}$ cycloalkenyl means a cycloalkenyl group having 3, 4, 5, 6, 7, 8, 9 or 10 carbon atoms and at least one double bond. In some embodiments, one or more of the hydrogen atoms in the cycloalkenyl groups can be optionally replaced with a halogen.

As used herein the term "alkenyl" refers to, whether it is used alone or as part of another group, straight or branched chain, unsaturated alkenyl groups. The term $C_{2-6}$ alkenyl means an alkenyl group having 2, 3, 4, 5, or 6 carbon atoms and at least one double bond. In some embodiments, one or more of the hydrogen atoms in the alkenyl groups can be optionally replaced with a halogen.

As used herein the term "heteroaryl" refers to cyclic groups that contain at least one aromatic ring and at least one heteroatom, such as N, O and/or S. The term $C_{5-10}$ heteroaryl means an aryl group having 5, 6, 7, 8, 9 or 10 atoms, in which at least one atom is a heteroatom, such as N, O and/or S. In some embodiments, one or more of the hydrogen atoms in the heteroaryl groups can be optionally replaced with a halogen.

In one embodiment, the compound is oxymorphone-3,14-diacetate. In another embodiment, the compound is 14-hydroxymorphinone-3,14-diacetate.

The metal catalyst can be any suitable catalyst capable of catalyzing the N-demethylation of a compound containing a tertiary N-methylamine in a continuous flow reactor system. In one embodiment, the catalyst is a transition metal catalyst. Examples of metal catalysts, include complexes and compounds, include, but are not limited to, catalysts comprising palladium, platinum (e.g., $PtCl_2$ and $K_2PtCl_4$), ruthenium (e.g., Ru/C, $RuCl_3H_2O$, $RuCl_2(PPh_3)_3$, $RuO_2$, tetrapropylammonium perruthenates), iron (e.g., $FeCl_2$, $FeSO_4$, and iron carbonyls such as $Fe_2(CO)_9$), tungsten (e.g., $Na_2WO_4$), vanadium (e.g., $VO(acac)_2$), iridium, copper, gold and silver complexes, or combinations thereof. In one embodiment, the catalyst is a Pd(0) or Pd(II) catalyst, for example, but not limited to $Pd(OAc)_2$, $Pd(acac)_2$, Pd black or palladium-perovskites, or Pd(0) or Pd(II) catalysts on any type of solid support (e.g., charcoal, sulfates, carbonates, alumina) or in encapsulated form, or combinations thereof.

In other embodiment, the palladium or platinum catalyst can include any palladium or platinum catalyst capable of catalyzing the N-demethylation of a compound containing a tertiary N-methylamine in a continuous flow reactor system. The catalyst can include palladium (0), platinum (0) or combinations thereof. The catalyst can include a catalyst, or catalyst precursor, that can be converted to palladium (0), platinum (0) or combinations thereof. The catalyst, or catalyst precursor can include $Pd(OAc)_2$, $PdCl_2$, $PdCl_2(PPh_3)_4$, $PdBr_2$, $Pd(acac)_2$, $Pd2(dba)_3$, $Pd(dba)_2$, $Pd(PPh_3)_4$, or combinations thereof.

The amount of catalyst can vary depending on the compound, reaction conditions, etc. The catalyst can be present in the liquid or reaction mixture in about 0.005 equivalents, 0.01 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5 or about 5 equivalents of the compound containing a tertiary N-methylamine. These values can also be used to define a range, such as about 0.01 equivalents to about 0.05 equivalents, or about 0.02 equivalents to about 0.04 equivalents.

The liquid or reaction mixture can contain variable amounts of the compound containing a tertiary N-methylamine and catalyst. The amount of the compound containing a tertiary N-methylamine in the liquid or reaction mixture can be about 0.05, 0.1, 0.15, 0.2, 0.25, 0.3, 0.35, 0.4, 0.45, 0.5, 0.6, 0.7, 0.8, 0.9 or about 1 M. These values can be used to define a range, such as about 0.25 to about 0.5 M. The amount of catalyst loading in the liquid or reaction mixture can be about 0.5 mol %, 1, 2, 3, 4, 5, 6, 7, 8, 9, 10, 11, 12, 13, 14, 15, 16, 17, 18, 19 or about 20 mol % of the tertiary N-methylamine compound. These values can be used to define a range, such as about 5 to about 10 mol %.

The liquid mixture can be provided in a solvent that contains the compound containing a tertiary N-methylamine and catalyst. The solvent can be any solvent capable of containing and providing a medium for the N-demethylation of the compound containing a tertiary N-methylamine in a continuous flow reactor system. The solvent can include dioxane, MeCN, i-PrOH, dimethyl sulfoxide (DMSO), dimethyl carbonate (DMC), N-methylpyrrolidone (NMP), dimethylacetamide (DMA), dimethylformamide (DMF) and combinations thereof. In one embodiment, the solvent includes dimethylformamide, dimethylsulfoxide, N-methylpyrrolidone, dimethylacetamide or combinations thereof. In another embodiment, the solvent includes dimethylacetamide.

The flow rate of the liquid mixture can vary depending on the dimensions of the continuous flow reactor system and to maintain efficient conversion and formation of the N-demethylated compound. The liquid mixture flow rate can be about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90 or 100 mL/min. On commercial scales, the flow rate can be as high as about 1 L/min or greater. These values can also be used to define a range, such as about 0.5 to about 1 mL/min.

The liquid mixture can be contacted with a gaseous oxidant or an organic peroxide oxidant to form a reaction mixture. The gaseous oxidant can be any oxidant capable of promoting N-demethylation of the compound containing a tertiary N-methylamine in a continuous flow reactor system. The oxidant can be air or molecular oxygen. In one embodiment, the oxidant is oxygen gas. The organic peroxide oxidant can be any oxidant capable of promoting N-demethylation of the compound containing a tertiary N-methylamine in a continuous flow reactor system. The organic peroxide oxidant can be t-butyl hydroperoxide.

The amount of oxidant can vary depending on the compound, reaction conditions, etc. The oxidant can be present in about 0.1 equivalents, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 or about 25 equivalents of the compound containing a tertiary N-methylamine. These values can also be used to define a range, such as about 1 equivalent to about 17 equivalents, or about 2 equivalents to about 10 equivalents.

The flow rate of the gaseous oxidant can vary depending on the dimensions of the continuous flow reactor system and to maintain efficient conversion and formation of the N-demethylated compound. The oxygen stream flow rate can be about 1, 5, 10, 20, 30, 40, 50, 60, 70, 80, 90 or about 100 mL/min. These values can also be used to define a range, such as about 5 to about 10 mL/min.

The process of the present disclosure can further include preparing a liquid mixture of the compound containing a tertiary N-methylamine and a palladium or platinum catalyst, or catalyst precursor, and reacting the catalyst or catalyst precursor to form Pd(0) or Pt(0). The preparation and reaction of the liquid mixture can occur before introduction of the liquid mixture to the continuous flow reactor system. Alternatively, the continuous flow system can include an on-line or in-line preparation section or segment (e.g., heating coil) to incorporate these steps into the reactor system. The reaction can include heating the liquid mixture for a predetermined time, adding one or more additives or stabilizers to the liquid mixture or combinations thereof.

The liquid mixture containing the catalyst or catalyst precursor can be heated to about 70° C., 80, 90, 100, 110, 120, 130, 140, 150, 160, 170, 180, 190 or about 200° C. These values can also be used to define a range, such as about 120° C. to about 140° C. The temperature can also be a few degrees (e.g., 1-10 degrees) below the degradation temperature of the tertiary N-methylamine compound. The temperature can also be the temperature or a few degrees (e.g., 1-10 degrees) above the temperature at which the catalyst or catalyst precursor forms Pd(0) or Pt(0). The liquid mixture containing the catalyst or catalyst precursor can be heated for about 0.5 min, 1, 2, 3, 4, 5, 6, 7, 8, 9, 10, 30 or about 60 minutes. These values can also be used to define a range, such as about 2 to about 10 minutes. The predetermined time can be dependent on the temperature and other conditions, and can be a time at which a substantial amount of the catalyst or catalyst precursor forms Pd(0) or Pt(0).

The liquid mixture, the reaction mixture, or both can contain an additive. The additive can be added to the liquid mixture before or after a pre-heating step. The additive can be any compound that stabilizes the catalyst, such as preventing or reducing the catalyst from agglomerating. The additive can be $C_1$-$C_{10}$ carboxylic acid. In one embodiment, the additive is acetic acid. The additive can be present in the liquid and reaction mixture in about 1 equivalent, 2, 3, 4, 5, 6, 7, 8, 9 or about 10 equivalents of the compound containing a tertiary N-methylamine. These values can also be used to define a range, such as about 1 to about 4 equivalents.

In some embodiments, the formation of the N-demethylated compound of formula (I) can have the respective formula (II), wherein the Y is selected from the group consisting of H, $C_{1\text{-}10}$ alkyl and C(O)—$C_{1\text{-}10}$ alkyl.

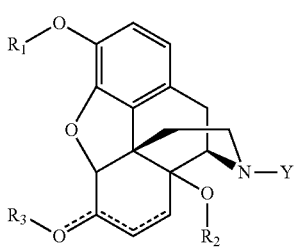

(II)

The process can further include a step of hydrogenating the N-demethylated compound. Standard hydrogenation process and method known to one skilled in the art can be used. After the reaction(s), the formed N-demethylated compound can be isolating by traditional purification, separation or isolation methodology, including chromatography, crystallization, extraction, precipitation, filtration, or combinations thereof.

In yet another embodiment, the present disclosure relates to a process for the preparation of a compound of formula (II)

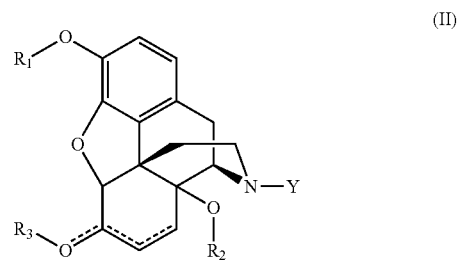

(II)

comprising reacting a compound of formula (I) with a metal catalyst in the presence of an oxidant;

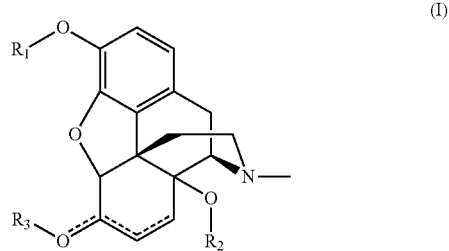

(I)

to provide a demethylated compound, wherein the Y is selected from the group consisting of H; or H and $C_{1\text{-}10}$ alkyl; or H and C(O)—$C_{1\text{-}10}$ alkyl; or H, $C_{1\text{-}10}$ alkyl, and C(O)—$C_{1\text{-}10}$ alkyl;

each ══ independently represents a single or double bond, provided that two double bonds are not adjacent to each other;

$R_1$ and $R_3$ are each independently selected from the group consisting of C(O)$R_4$, $C_{1\text{-}10}$ alkyl, $C_{6\text{-}10}$ aryl, $C_{3\text{-}10}$ cycloalkyl, alkylene-$C_{6\text{-}10}$ aryl, $C_{1\text{-}10}$ alkylene-$C_{3\text{-}10}$ cycloalkyl, and PG;

$R_2$ is selected from the group consisting of C(O)$R_4$, S(O)$R_4$, SO$_2R_4$, P(O)$R_4R_5$, P(O)(O$R_4$)$R_5$, and P(O)(O$R_4$)(O$R_5$), and $R_4$ and $R_5$ are each independently selected from $C_{3\text{-}10}$ cycloalkyl, $C_{3\text{-}10}$ heterocycloalkyl, $C_{3\text{-}10}$ cycloalkenyl, $C_{1\text{-}10}$ alkyl, $C_{2\text{-}10}$ alkenyl, $C_{6\text{-}10}$ aryl and $C_{5\text{-}10}$ heteroaryl, each of the latter groups being unsubstituted or substituted with one or more substituents independently selected from $C_{1\text{-}4}$ alkyl, O$C_{1\text{-}4}$ alkyl, halo, CN, NO$_2$, $C_{6\text{-}10}$ aryl and O$C_{6\text{-}10}$ aryl;

further reacting the demethylated compound by standard processes, e.g., hydrogenation, dehydrogenation, etc., to form the compound of formula (II), wherein the Y is selected from the group consisting of H; or H and $C_{1\text{-}10}$ alkyl; or H and C(O)—$C_{1\text{-}10}$ alkyl; or H, $C_{1\text{-}10}$ alkyl, and C(O)—$C_{1\text{-}10}$ alkyl.

The process of the present disclosure can efficiently convert the tertiary N-methylamine compound to the desired N-demethylated compound in a high yield. The percent conversion of the tertiary N-methylamine compound can be greater than about 50%, 55%, 60%, 65%, 70%, 75%, 80%, 85%, 90%, 91%, 92%, 93%, 94%, 95%, 96%, 97%, 98% or about 99%. These values can also define a range, such as about 92% to about 98%. The yield of the desired N-demethylated compound can be greater than about 70%, 71%, 72%, 73%, 74%, 75%, 76%, 77%, 78%, 79%, 80%, 80%, 81%, 82%, 83%, 84%, 85%, 86%, 87%, 88%, 89%, 90%, 91%, 92%, 93%, 94%, 95%, 96%, 97%, 98% or about 99%. These values can define a range, such as about 90% to about 99%.

These conversion and yields can be obtained in a relatively short time. The conversion of the tertiary N-methylamine compound and/or the formation of the desired N-demethylated compound in a high yield can be achieved in less than about 24 hours, 18, 16, 12, 10, 9, 8, 7, 6, 5, 4, 3, 2, 1, 0.9, 0.8, 0.7, 0.6, 0.5, 0.4, 0.3, 0.2 or about 0.1 hours. These values can also be used to define a range, such as about 0.3 to about 1 hour.

The process of the present disclosure can be performed in a continuous manner. The continuous flow system, one or more of the reactions in the continuous flow system, or combinations thereof can be carried out under elevated temperature. For example, the reaction can occur in one or more residence time units (RTU) each independently having a length of tubing or coil and heated to an elevated temperature. The length of tubing or coil can be characterized by volume. The length of tubing or coil can contain a volume of about 1 mL, 2, 3, 4, 5, 6, 7, 9, 10, 15, 20, 25, 30, 35, 40, 45, 50, 100, 150, 200, 250, 300, 400, 500, 600, 700, 800, 900 or about 1000 mL. These values can also be used to define a range, such as about 5 to about 50 mL. The temperature of each RTU unit can be about 80, 90, 100, 110, 120, 130, 140, 150, 160, 170, 180, 190 or about 200° C. These values can also be used to define a range, such as about 120° C. to about 140° C. The temperature can also be a few degrees (e.g., 1-10 degrees) below the degradation temperature of the reagents or desired products.

In the continuous flow system, one or more of the reactions in the continuous flow system, or combinations thereof can be carried out under elevated pressure. The system pressure can be maintained by one or more pumps and back pressure regulators contained in the system. The system pressure can be about 2, 3, 4, 5, 6, 7, 8, 9, 10, 15, 20, 25, 30, 35, 40, 45, 50, 60, 70, 80, 90 or about 100 bar. These values can also be used to define a range, such as about 5 to about 25 bar.

The size and material of the tubing containing the liquid mixture and/or throughout the continuous flow reactor system can also vary depending on the type of reagents used, products produced and to maintain efficient conversion and formation of the selectively reduced compound. The size of the tubing can be about 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90 or about 100 mm i.d. These values can also be used to define a range, such as about 0.8 to about 1 mm i.d. The material of the tubing can be an inert plastic, such as perfluoroalkoxy, a composite material, a metal, such as stainless steel, a nickel based alloy (e.g., hastelloy), or combinations thereof.

In particular embodiments, the present disclosure relates to a scalable process for the aerobic, palladium-catalyzed N-demethylation of a morphinan alkaloid, e.g., oxymorphone 3,14-diacetate or 14-hydroxymorphinone 3,14-diacetate, to their nor-derivatives. The process includes the use of palladium(II) acetate which forms colloidal palladium(0) particles upon heating in N,N-dimethlyacetamide. The palladium(0) particles are catalysts for the aerobic N-demethylation of the opiate alkaloids. The N-demethylation of 14-hydroxymorphinone 3,14-diacetate with molecular oxygen as the oxidant in a continuous flow reactor can provide the N-demethylated products with excellent selectivity after residence times of 10 to 20 min with 2.5 to 5 mol % of palladium acetate as catalyst. Subsequent hydrogenation with molecular hydrogen in a packed bed reactor can afford 3,14-diacetyl-noroxymorphone.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

N-Demethylation of Oxymorphone 3,14-Diacetate

Figure 3:
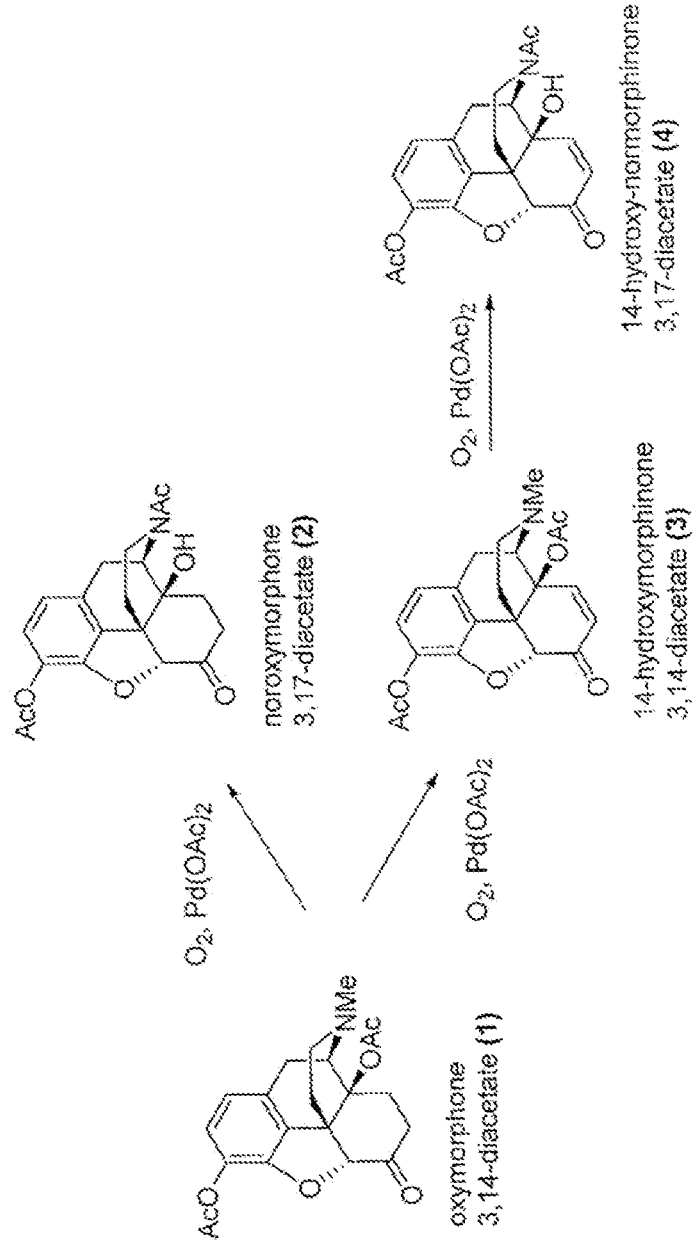
FIG. 3 shows synthesis routes for palladium (e.g., Pd(OAc)$_2$) catalyzed aerobic N-demethylation/dehydrogenation of oxymorphone 3,14-diacetate.

The N-demethylation of oxymorphone 3,14-diacetate was performed using a palladium catalyst under aerobic conditions. FIG. 3 shows the synthesis routes for palladium (e.g., $Pd(OAc)_2$) catalyzed aerobic N-demethylation/dehydrogenation of oxymorphone 3,14-diacetate (1). Oxymorphone 3,14-diacetate (1) can be synthesized by well-developed procedures starting from the naturally occurring opiates oripavine and thebaine. Hydroxylation of oripavine at position C14 provides 14-hydroxymorphinone, which in turn can be hydrogenated and acetylated to give the oxymorphone 3,14-diacetate.

The N-demethylation of oxymorphone 3,14-diacetate was performed in a microwave batch reactor. 50 mg or 100 mg of oxymorphone 3,14-diacetate (0.13 mmol), $Pd(OAc)_2$ at a catalyst loading of 5 or 10 mol % of $Pd(OAc)_2$ and 1 mL of a solvent were filled into a 5 mL microwave vessel. The various solvents used included dioxane, MeCN, i-PrOH, dimethyl sulfoxide (DMSO), dimethyl carbonate (DMC) and dimethylacetamide (DMA). The vessel was sealed with a septum and flushed with oxygen gas for several minutes. In some experiments, the mixture was stirred in the open air. The reaction was performed in a closed vial. The headspace of the microwave vessel (about 4 mL) provided about 0.16 mmol or 1.25 equiv of oxygen gas. After a reaction time of 15 min the vial was cooled to room temperature and the mixture analyzed by HPLC. The vial was again flushed with oxygen gas and subsequently heated again in the microwave reactor for an additional 25 min (40 total) and 40 min (80 total) and analyzed after each heating. The conversion data is based on the HPLC peak area at 215 nm. Full conversion of oxymorphone 3,14-diacetate was obtained after a reaction time of 80 min at 120° C. Tables 1 and 2 list the conversion data for the N-demethylation of oxymorphone 3,14-diacetate (1) to noroxymorphone 3,17-diacetate (2), 14-hydroxymorphinone 3,14-diacetate (3) and 14-hydroxy-normorphinone 3,17-diacetate (4) at different temperatures in the different solvents in a microwave reactor.

It was observed that lower reaction temperatures reduced the reaction rate and produced the dehydrogenated morphinan as the main product (conversions of about 7% were obtained after 90 min at 80° C.), while a further increase of the reaction temperature did not accelerate the reaction any further.

TABLE 1

N-demethylation of oxymorphone 3,14-diacetate at various conditions.

| entry | solvent | catalyst loading [mol %] | oxidant | temp. [° C.] | reaction time [min] | 1 [%] | 2 [%] | 3 [%] | 4 [%] |
|---|---|---|---|---|---|---|---|---|---|
| 1 | dioxane | 10 | O₂ | 80 | 30 | 97 | 0 | 3 | 0 |
|   |   |   |   |   | 90 | 93 | 0 | 7 | 0 |
| 2 | MeCN | 10 | O₂ | 80 | 30 | 85 | 11 | 3 | 0 |
|   |   |   |   |   | 90 | 44 | 28 | 3 | 8 |
| 3 | dioxane | 10 | air | 120 | 15 | 84 | 12 | 4 | 0 |
|   |   |   |   |   | 40 | 73 | 21 | 4 | 1 |
|   |   |   |   |   | 80 | 62 | 33 | 3 | 2 |
| 4 | dioxane | 10 | O₂ | 120 | 15 | 68 | 25 | 4 | 2 |
|   |   |   |   |   | 40 | 27 | 61 | 2 | 5 |
|   |   |   |   |   | 80 | 0 | 84 | 0 | 8 |
| 5 | dioxane | 10 | O₂ | 140 | 15 | 81 | 14 | 4 | 1 |
|   |   |   |   |   | 40 | 51 | 38 | 3 | 3 |
|   |   |   |   |   | 80 | 11 | 78 | 1 | 4 |
| 6 | dioxane | 5 | O₂ | 120 | 15 | 63 | 33 | 2 | 0 |
|   |   |   |   |   | 40 | 25 | 69 | 0 | 1 |
|   |   |   |   |   | 80 | 0 | 90 | 0 | 4 |
| 7 | dioxane | 5 | O₂ | 120 | 40 | 41 | 50 | 2 | 3 |
|   |   |   |   |   | 80 | 32 | 58 | 0 | 5 |
|   |   |   |   |   | 120 | 0 | 86 | 0 | 7 |
| 8 | i-PrOH | 10 | O₂ | 120 | 15 | 94 | 6 | 0 | 0 |
|   |   |   |   |   | 40 | 87 | 11 | 0 | 0 |
|   |   |   |   |   | 80 | 86 | 12 | 0 | 0 |
| 9 | DMSO | 10 | O₂ | 120 | 15 | 65 | 24 | 8 | 2 |
|   |   |   |   |   | 40 | 34 | 53 | 5 | 6 |
|   |   |   |   |   | 80 | 5 | 80 | 1 | 10 |
| 10 | DMSO | 10 | O₂ | 140 | 14 | 58 | 33 | 2 | 3 |
|   |   |   |   |   | 40 | 39 | 59 | 3 | 4 |
|   |   |   |   |   | 80 | 30 | 61 | 4 | 5 |
| 11 | DMC | 10 | O₂ | 120 | 15 | 59 | 38 | 2 | 2 |
|   |   |   |   |   | 40 | 40 | 56 | 2 | 3 |
|   |   |   |   |   | 80 | 10 | 83 | 0 | 4 |
| 12 | DMA | 10 | O₂ | 120 | 15 | 32 | 61 | 1 | 2 |
|   |   |   |   |   | 40 | 0 | 88 | 0 | 4 |

TABLE 2

N-demethylation of oxymorphone 3,14-diacetate at 120° C. in dioxane.

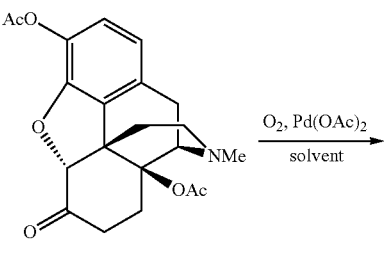

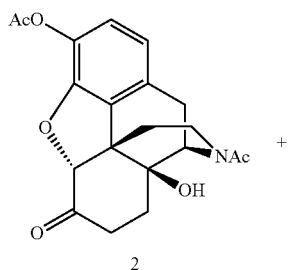

| reaction time [min] | 1 [%] | 2 [%] | 3 [%] | 4 [%] | others [%] |
|---|---|---|---|---|---|
| 15 | 63 | 33 | 2 | 0 | 2 |
| 40 | 25 | 69 | 0 | 1 | 5 |
| 80 | 0 | 90 | 0 | 4 | 6 |

The desired product was noroxymorphone 3,17-diacetate (2) which is a N-acetyl derivative formed by N-demethylation and subsequent intramolecular O- to N-acetyl migration (See FIG. 3). At the 120° C. reaction temperature, the catalyst loading can be reduced to 5 mol % Pd(OAc)₂ without reducing the reaction rate appreciably. The N-demethylation reaction was very clean with a selectivity of >90% for the desired product (2). The main side-products were 14-hydroxymorphinone 3,14-diacetate (3) and the unsaturated N-acetyl compound (4). 14-hydroxymorphinone 3,14-diacetate is produced by a Pd(OAc)₂-catalyzed aerobic dehydrogenation of the oxymorphone 3,14-diacetate to the corresponding enone. The 14-hydroxymorphinone 3,14-diacetate underwent slow N-demethylation and concomitant acetyl migration to generate the unsaturated N-acetyl compound. The noroxymorphone 3,17-diacetate, on the other hand, is stable under the reaction conditions and is not oxidized further to the α,β-unsaturated ketone, even after extended reaction times. Table 3 lists the conversion data for the N-demethylation of oxymorphone 3,14-diacetate at 120° C. for extended reaction times.

100 mg of oxymorphone 3,14-diacetate (0.26 mmol), 5 mol % of Pd(OAc)₂ and 1 mL of a solvent were combined. The reactions were performed on a hot-plate with oxygen gas bubbled through the solution, or the mixture was stirred in an open vial (air). The reaction was performed in a closed vial.

TABLE 3

N-demethylation of oxymorphone 3,14-diacetate at 120° C. for extended reaction times.

| entry | solvent | catalyst loading [mol %] | oxidant | temp. [° C.] | reaction time [min] | 1 [%] | 2 [%] | 3 [%] | 4 [%] |
|---|---|---|---|---|---|---|---|---|---|
| 1 | DMA | 5 | air | 120 | 35 | 40 | 56 | 1 | 3 |
|   |   |   |   |   | 95 | 0 | 96 | 0 | 4 |
|   |   |   |   |   | 180 | 0 | 95 | 0 | 5 |
| 2 | DMA | 5 | closed | 120 | 40 | 81 | 15 | 3 | 1 |
|   |   |   |   |   | 120 | 74 | 23 | 2 | 1 |
| 3 | DMF | 5 | air | 120 | 35 | 52 | 45 | 2 | 2 |
|   |   |   |   |   | 95 | 10 | 87 | 0 | 3 |
| 4 | DMF | 0 | O₂ | 120 | 35 | 99 | 0 | 1 | 0 |
|   |   |   |   |   | 140 | 96 | 2 | 1 | 0 |
| 5 | NMP | 5 | air | 120 | 35 | 48 | 48 | 2 | 2 |
|   |   |   |   |   | 95 | 13 | 83 | 0 | 4 |

Example 2

Stabilization of the Palladium Catalyst

The palladium catalyzed aerobic N-demethylation of oxymorphone 3,14-diacetate was performed in the presence of different additives to stabilize the catalyst, including stabilizing the Pd(0), once formed, from precipitation. In the oxidation reactions described in the present disclosure, the Pd(0) can irreversibly agglomerate to metallic palladium. In the reactions of Example 1, it was observed that metallic Pd precipitated on the wall of the reaction vessel almost immediately after the reaction mixture was heated. The precipitation of Pd black can cause problems in a flow reactor.

The initial additives tested were pyridine and tetrabutylammonium bromide (TBAB). 50 mg of oxymorphone 3,14-diacetate (0.13 mmol), 0.1 or 1 equivalent of the additive and 10 mol % of Pd(OAc)$_2$ were added in 1 mL of dioxane. The reaction was run for 80 min at a reaction temperature of 120° C. The reactions were performed in a microwave reactor as described in Example 1. Table 4 lists the conversion data for the N-demethylation of oxymorphone 3,14-diacetate at 120° C. in the presence of additives.

TABLE 4

N-Demethylation of Oxymorphone 3,14-Diacetate at 120° C. in the Presence of Additives.

| entry | additive (equiv) | 1 [%] | 2 [%] | 3 [%] | 4 [%] | others [%] |
|---|---|---|---|---|---|---|
| 1 | none | 0 | 84 | 0 | 8 | 8 |
| 2 | Pyridine (1) | 49 | 0 | 51 | 0 | 0 |
| 3 | Pyridine (0.1) | 73 | 10 | 12 | 4 | 1 |
| 4 | TBAB (0.1) | 80 | 2 | 12 | 6 | 0 |

One equivalent of the pyridine additive with respect to the oxymorphone 3,14-diacetate stabilized the palladium and no formation of Pd black was observed. However, the only product formed was 14-hydroxymorphinone 3,14-diacetate (3) and no N-demethylation was observed. Reducing the amount of the pyridine additive to 10 mol % (with respect to the oxymorphone 3,14-diacetate) did not prevent the formation of metallic Pd, and reduced the reaction rate. A mixture of the N-demethylated (2) and the dehydrogenated products (3) and (4) were formed. The use of 10 mol % (0.1 equivalent) of tetrabutylammonium bromide also reduced the reaction rate and produced mixtures of the demethylated and dehydrogenated products.

Several protic and polar aprotic solvents were then tested, including i-PrOH, DMSO, DMC and DMA. Similar to pyridine, DMSO can promote the re-oxidation of Pd(0) to Pd(II) and reduce or prevent its precipitation as metallic palladium. 50 mg of oxymorphone 3,14-diacetate (0.13 mmol), 10 mol % of Pd(OAc)$_2$ and 1 mL of solvent were combined. The reaction was run for 40 or 80 min at a reaction temperature of 120° C. The reactions were performed in a microwave reactor as described in Example 1. Table 5 lists the conversion data for the N-demethylation of oxymorphone 3,14-diacetate at 120° C. in different stabilizing solvents.

TABLE 5

N-Demethylation of Oxymorphone 3,14-Diacetate at 120° C. in the Different Stabilizing Solvents.

| entry | solvent | reaction time [min] | 1 [%] | 2 [%] | 3 [%] | 4 [%] | others [%] |
|---|---|---|---|---|---|---|---|
| 1 | i-PrOH | 80 | 86 | 12 | 0 | 0 | 2 |
| 2 | DMSO | 80 | 5 | 80 | 1 | 10 | 4 |
| 3 | DMC | 80 | 10 | 83 | 0 | 4 | 3 |
| 4 | DMA | 40 | 0 | 88 | 0 | 4 | 8 |

With polar aprotic solvents, such as DMSO and DMA, the reaction mixture became dark during heating, indicating the formation of Pd(0). However, the colloidal palladium remained dispersed in solution throughout the reaction and did not precipitate on the vessel wall. DMA provided the fastest reaction time with complete conversion of oxymorphone 3,14-diacetate after about 40 min at 120° C. It was observed that the reaction rate decreased when the scale of the reaction was increased to 100 mg under similar conditions (See Entry 7, Table 2). About 120 min at 120° C. were required for full conversion. As shown in Table 5, the reaction rate was restored on the 100 mg scale by bubbling oxygen gas through the reaction solution as performed on the hot plate, similar to continuous flow reaction conditions. The combination of 100 mg of oxymorphone 3,14-diacetate and only 5 mol % of Pd(OAc)$_2$ in 1 mL DMA resulted in full conversion after about 40 min at 120° C. (e.g., 88% selectivity according to HPLC).

Additional observations regarding the palladium catalyzed aerobic N-demethylation of oxymorphone 3,14-diacetate include that the reaction can be performed with atmospheric oxygen. See Tables 2 and 3. For experiments using atmospheric oxygen, the reaction mixture was stirred in an open vial at 120° C. The reaction rate was slower under these conditions, but the selectivity of the reaction was substantially the same as compared to oxygen gas.

The influence of water on the reaction was also studied. The N-demethylation reaction can start by coordination of a Pd(II) species to the nitrogen, followed by a β-hydride elimination to generate an iminium cation and Pd(0). Hydrolysis of the iminium ion by water can form the secondary amine and formaldehyde. 100 mg of oxymorphone 3,14-diacetate (0.26 mmol), 5 mol % of Pd(OAc)$_2$ and 1 mL DMA were combined. The reaction was run at a reaction temperature of 120° C. in the presence of differing amounts of water. The reactions were performed on a hot-plate with oxygen gas bubbled through the solution. The presence of water decreases both reaction rate and selectivity of the N-demethylation reaction. In some embodiments, the continuous flow reactor system and/or the reactions can be performed in a moisture free or substantially moisture free environment.

TABLE 6

N-Demethylation of Oxymorphone 3,14-Diacetate in DMA at 120° C. in the Presence of Water.

| H$_2$O [μL] | 1 [%] | 2 [%] | 3 [%] | 4 [%] | others [%] |
|---|---|---|---|---|---|
| 0 | 8 | 74 | 0 | 12 | 6 |
| 10 | 57 | 21 | 13 | 9 | 0 |
| 50 | 72 | 10 | 14 | 4 | 0 |

Example 3

Continuous Flow N-Demethylation of Oxymorphone 3,14-Diacetate

Figure 4:
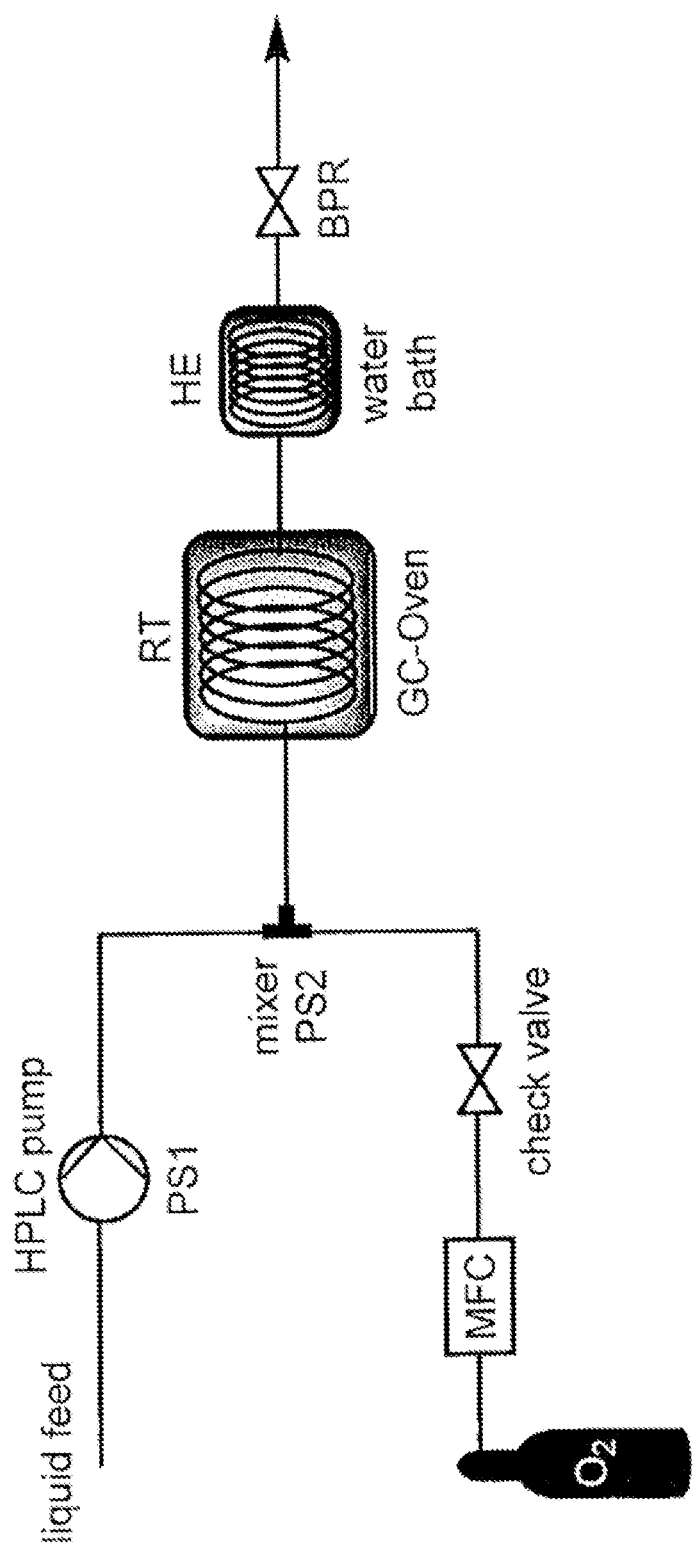
FIG. 4 shows an exemplary illustration of the continuous flow reactor system: PS=pressure sensor, MFC=mass flow controller, BPR=back-pressure regulator.

The palladium catalyzed aerobic N-demethylation of oxymorphone 3,14-diacetate was performed in a continuous flow reactor system. FIG. 4 shows an exemplary illustration of the continuous flow reactor system. The continuous flow reactor system included an HPLC pump to pump the liquid feed or liquid mixture. The liquid mixture was pumped into a mixing unit that can be temperature controlled, or be maintained at room temperature. In the mixing unit, the liquid mixture was combined with oxygen gas fed from a gas cylinder. The combined gas-liquid stream, or reaction mixture, was then pumped through a heated residence tube (RT) heated by a GC-oven. The reaction mixture was then cooled by pumping through a short residence tube in a water bath (HE). The reaction mixture exited the reactor system through a back-pressure regulator (BPR).

The liquid mixture included variable amounts of oxymorphone 3,14-diacetate and catalyst dissolved in a variety solvents. The liquid mixture was pumped at about 0.5 mL/min. The oxygen gas was pumped at about 5 mL/min (measured at normal conditions, i.e., T=0° C. and p=1 atm). The continuous flow reactor system was held at an elevated pressure of about 15 bar. At this pressure and these flow rates, the oxygen gas was substantially or completely dissolved in the reaction mixture and no gas phase was visible at room temperature. At higher flow rates of the gas, discrete gas/liquid segments were formed in the residence tube. Flow experiments were performed using different mixer geometries and tube reactors made of either perfluoroalkoxy alkane (PFA) or stainless steel with residence volumes of 10, 20 or 25 mL. The solvents used were either DMA or dimethylformamide (DMF). The pressures tested ranged from atmospheric to about 20 bar and residence times ranged between about 8 to about 40 min. The oxidant was either synthetic air or oxygen gas. The stoichiometries of the oxidant varied in the range from 0 to 17 equiv.

200 mg of oxymorphone 3,14-diacetate (0.52 mmol), 5 mol % Pd(OAc)$_2$ and 2 mL DMA or DMF were combined. The oxidant was either oxygen gas or air controlled by a mass flow controller. Tables 7 and 8 list the conversion data for the N-demethylation of oxymorphone 3,14-diacetate under continuous flow conditions. For entries 8-10 in Table 7 and entries 17-19 in Table 8, the reaction mixture was heated on a hot plate before introduction to the continuous flow reaction system for about 2 min at 90° C.

TABLE 7

N-Demethylation of Oxymorphone 3,14-Diacetate under Continuous Flow Conditions.

| entry | reactor/ volume [mL] | solvent/flow rate [mL/min] | gas/flow rate [mL$_N$/min] | stoich. | temp [° C.] | p [bar] | RT [min] | 1 [%] | 2 [%] | 3 [%] | 4 [%] |
|---|---|---|---|---|---|---|---|---|---|---|---|
| 1 | PFA/25 | DMA/0.6 | O$_2$/60 | 17.0 | 120 | 13 | 6 | 67 | 14 | 15 | 3 |
| 2 | PFA/25 | DMA/0.5 | O$_2$/30 | 10.0 | 120 | 9 | 7 | 68 | 13 | 15 | 3 |
| 3 | PFA/25 | DMF/0.5 | O$_2$/30 | 10.0 | 120 | 9 | 7 | 69 | 13 | 15 | 3 |
| 4 | PFA/25 | DMF/0.5 | O$_2$/20 | 6.9 | 120 | 9 | 22 | 67 | 13 | 16 | 5 |
| 5 | PFA/25 | DMF/0.5 | O$_2$/10 | 3.4 | 120 | 7 | 24 | 64 | 13 | 17 | 6 |
| 6 | PFA/25 | DMF/0.5 | O$_2$/5 | 1.7 | 120 | 7 | 33 | 66 | 13 | 16 | 6 |
| 7 | PFA/25 | DMF/1.0 | O$_2$/0 | 0.0 | 120 | 9 | 22 | 82 | 16 | 2 | 0 |
| 8 | SS/20 | DMF/0.5 | O$_2$/10 | 3.4 | 120 | 11 | 24 | 52 | 39 | 3 | 5 |
| 9 | SS/20 | DMA/0.5 | O$_2$/6 | 2.1 | 130 | 11 | 21 | 17 | 61 | 2 | 17 |
| 10 | SS/20 | DMA/0.5 | O$_2$/6 | 2.1 | 140 | 10 | 23 | 0 | 73 | 0 | 22 |

TABLE 8

N-Demethylation of Oxymorphone 3,14-Diacetate under Continuous Flow Conditions

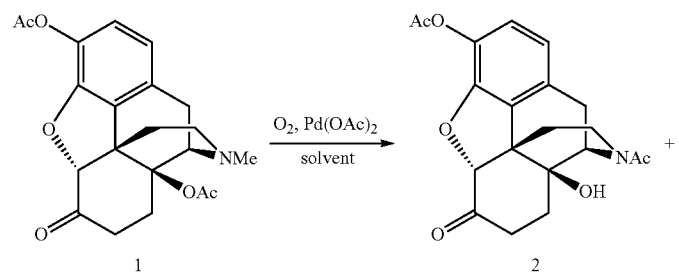

TABLE 8-continued

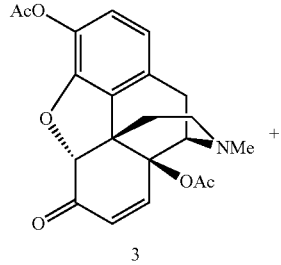

| entry | reactor/volume [mL] | solvent/flow rate [mL/min] | gas/flow rate [mL_N/min] | stoich. | temp [° C.] | p [bar] | RT [min] | 1 [%] | 2 [%] | 3 [%] | 4 [%] |
|---|---|---|---|---|---|---|---|---|---|---|---|
| 1 | PFA/25 | DMA/0.5 | air/60 | 4.1 | 120 | 13 | 5 | 75 | 11 | 14 | 0 |
| 2 | PFA/25 | DMA/0.5 | air/30 | 2.1 | 120 | 12 | 9 | 63 | 18 | 15 | 4 |
| 3 | SS/20 | DMF/0.5 | air/20 | 1.4 | 120 | 11 | 14 | 73 | 12 | 12 | 3 |
| 4 | SS/20 | DMF/0.5 | air/20 | 1.4 | 120 | 7 | 7 | 77 | 13 | 8 | 2 |
| 5 | PFA/25 | DMA/0.6 | $O_2$/60 | 17.0 | 120 | 13 | 6 | 67 | 14 | 15 | 3 |
| 6 | PFA/25 | DMA/0.5 | $O_2$/30 | 10.0 | 120 | 9 | 7 | 68 | 13 | 15 | 3 |
| 7 | PFA/25 | DMF/0.5 | $O_2$/30 | 10.0 | 120 | 9 | 7 | 69 | 13 | 15 | 3 |
| 8 | PFA/25 | DMF/0.5 | $O_2$/20 | 6.9 | 120 | 9 | 22 | 67 | 13 | 16 | 5 |
| 9 | PFA/25 | DMF/0.5 | $O_2$/10 | 3.4 | 120 | 7 | 24 | 64 | 13 | 17 | 6 |
| 10 | PFA/25 | DMF/0.5 | $O_2$/5 | 1.7 | 120 | 7 | 33 | 66 | 13 | 16 | 6 |
| 11 | PFA/25 | DMF/1.0 | $O_2$/0 | 0.0 | 120 | 9 | 22 | 82 | 16 | 2 | 0 |
| 12 | SS/20 | DMF/0.5 | $O_2$/20 | 6.9 | 120 | 13 | 18 | 71 | 13 | 13 | 3 |
| 13 | SS/20 | DMF/0.5 | $O_2$/10 | 3.4 | 120 | 11 | 32 | 75 | 18 | 4 | 1 |
| 14 | SS/20 | DMF/1.0 | $O_2$/5 | 0.9 | 120 | 7 | 14 | 66 | 15 | 16 | 4 |
| 15 | SS/20 | DMF/1.0 | $O_2$/3 | 0.5 | 120 | 8 | 17 | 68 | 13 | 16 | 4 |
| 16 | SS/20 | DMF/2.0 | $O_2$/5 | 0.4 | 120 | 8 | 6 | 79 | 16 | 2 | 0 |
| 17 | SS/20 | DMF/0.5 | $O_2$/10 | 3.4 | 120 | 11 | 24 | 52 | 39 | 3 | 5 |
| 18 | SS/20 | DMA/0.5 | $O_2$/6 | 2.1 | 130 | 11 | 21 | 17 | 61 | 2 | 17 |
| 19 | SS/20 | DMA/0.5 | $O_2$/6 | 2.1 | 140 | 10 | 23 | 0 | 73 | 0 | 22 |

The majority of the results in Tables 7 and 8 for the continuous flow experiment did not reproduce the results obtained under the batch conditions of the prior examples (e.g., conversions, selectivities). The highest conversions were about 30-35%. Interestingly, formation of the dehydrogenated side products (3) and (4) was high when the amount of oxygen gas was reduced below 1 equivalent (See Entry 7, Table 7).

The oxymorphone 3,14-diacetate and Pd(OAc)$_2$ dissolved in DMA resulted in a yellowish to orange, transparent solution. Upon heating, the mixture quickly turned black due to the formation of fine palladium(0) particles. When the reaction was performed in the flow reactor without preheating, the processed reaction mixture kept its clear, orange appearance. The exceptions were experiments with <0.5 equiv of oxygen gas which resulted in black solutions during the reaction (See Entry 7, Table 7) and experiments with preheating of the liquid mixture about 2 min at 90° C. on a hot plate prior to the flow reaction. The black solutions in the later continuous flow experiments led to significantly better conversions (See Entries 8-10, Table 7 and Entries 17-19, Table 8). These results suggest that the catalytic cycle starts with a Pd(0) species, and a deficiency of oxygen is necessary for the catalytically active Pd(0) species to form from Pd(OAc)$_2$. Under the highly oxidative conditions in the flow reactor, the active Pd(0) species is not formed, or not formed in sufficient amounts, and the palladium remains in its Pd(II) state throughout the reaction.

Example 4

N-Demethylation of 14-Hydroxymorphinone 3,14-Diacetate

Figure 5:
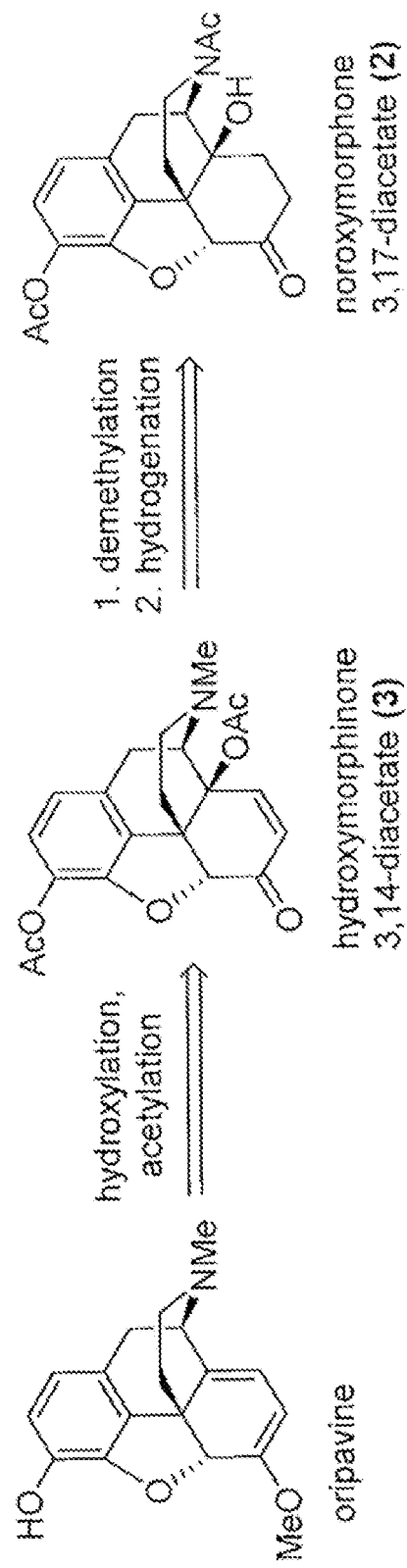
FIG. 5 shows an exemplary palladium (e.g., Pd(OAc)$_2$) catalyzed aerobic N-demethylation/dehydrogenation of hydroxymorphinone 3,14-diacetate.
Figure 6:
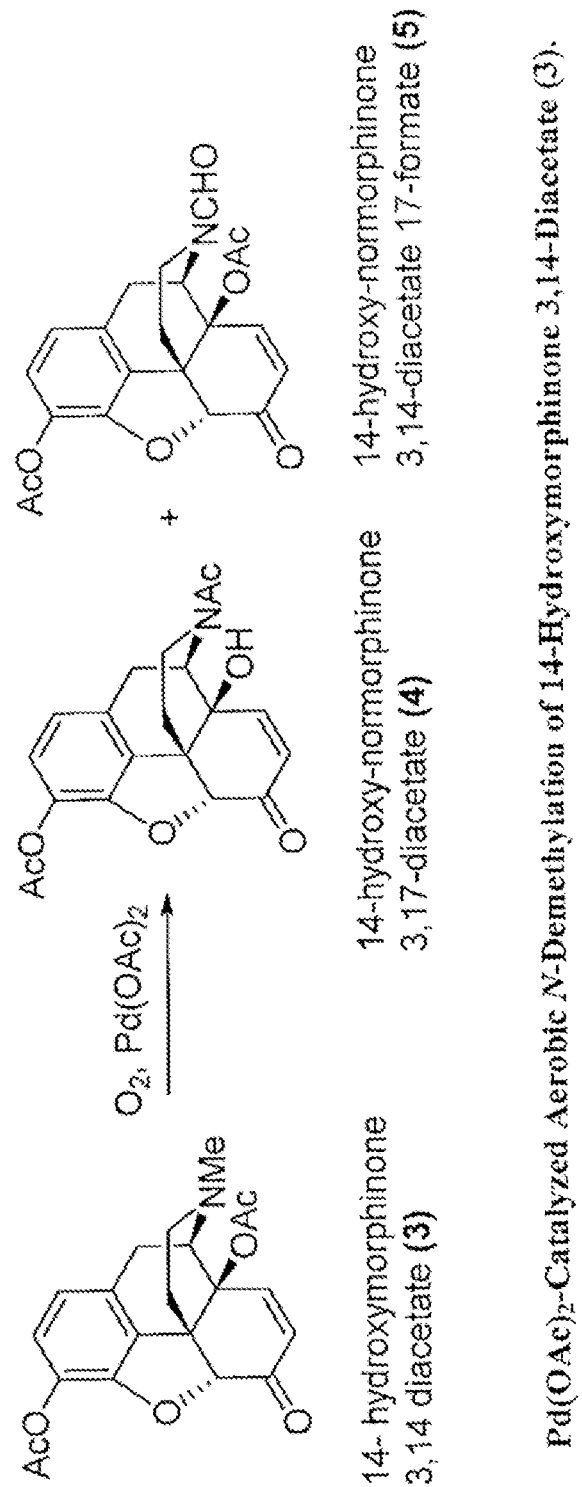
FIG. 6 shows an exemplary palladium (e.g., Pd(OAc)$_2$) catalyzed aerobic N-demethylation of 14-hydroxymorphinone 3,14-diacetate.

The palladium catalyzed aerobic N-demethylation of hydroxymorphinone 3,14-diacetate was performed. FIGS. 3, 5 and 6 show exemplary illustrations of the synthesis. Hydrogenation of the enone double bond of the nor-derivative formed, i.e., 14-hydroxy-normorphinone 3,17-diacetate (4), can produce the desired product, noroxymorphone 3,17-diacetate (2).

100 mg of hydroxymorphinone 3,14-diacetate (0.26 mmol), 5 mol % of Pd(OAc)$_2$ and 1 mL of solvent were combined. The reaction was run at a reaction temperature of 120° C. The reactions were performed on a hot-plate either in an open vial (air) or with oxygen gas bubbled through the solution. Tables 9 and 10 list the conversion data for the N-demethylation of hydroxymorphinone 3,14-diacetate.

TABLE 9

N-Demethylation of 14-Hydroxymorphinone 3,14-Diacetate with Air or Oxygen Gas as Oxidant at 120° C. (90 min Reaction Time).

| entry | solvent | oxidant | 3 [%] | 4 [%] | 5 [%] |
|---|---|---|---|---|---|
| 1 | DMF | air | 64 | 36 | 0 |
| 2 | DMF | $O_2$ | 7 | 90 | 2 |
| 3 | DMA | air | 62 | 38 | 0 |
| 4 | DMA | $O_2$ | 0 | 97 | 3 |

TABLE 10

N-Demethylation of 14-Hydroxymorphinone 3,14-Diacetate on a Hot-Plate.

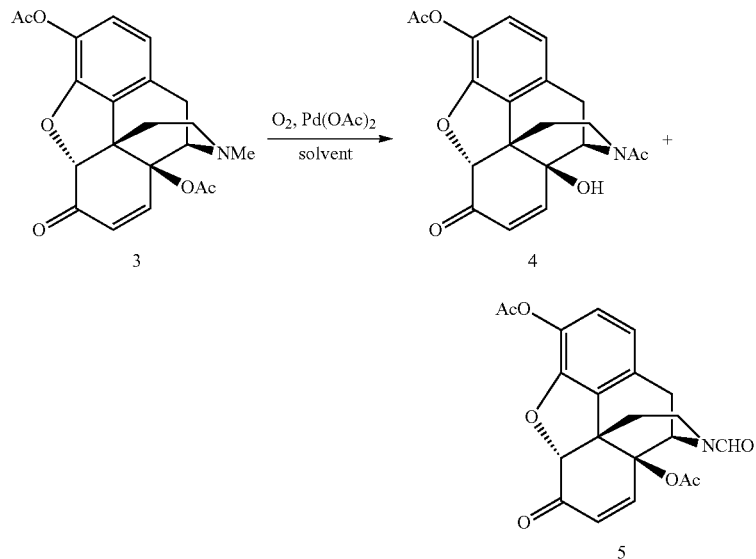

| entry | solvent | catalyst loading [mol %] | oxidant | temp. [° C.] | reaction time [min] | 3 [%] | 4 [%] | 5 [%] |
|---|---|---|---|---|---|---|---|---|
| 1 | DMF | 5 | air | 120 | 30 | 81 | 19 | 0 |
|   |     |   |     |     | 90 | 64 | 36 | 0 |
|   |     |   |     |     | 360 | 32 | 67 | 0 |
| 2 | DMF | 5 | $O_2$ | 120 | 30 | 72 | 28 | 0 |
|   |     |   |     |     | 90 | 7 | 90 | 2 |
|   |     |   |     |     | 360 | 0 | 96 | 3 |
| 3 | DMA | 5 | air | 120 | 35 | 79 | 20 | 0 |
|   |     |   |     |     | 95 | 62 | 38 | 0 |
| 4 | DMA | 5 | $O_2$ | 120 | 35 | 29 | 67 | 3 |
|   |     |   |     |     | 95 | 0 | 97 | 3 |
| 5 | MeCN | 5 | air | 75 | 35 | 95 | 5 | 0 |
|   |     |   |     |     | 100 | 94 | 6 | 0 |
|   |     |   |     |     | 190 | 93 | 7 | 0 |
| 6 | i-PrOH | 5 | air | 75 | 35 | 100 | 0 | 0 |
|   |     |   |     |     | 100 | 100 | 0 | 0 |
|   |     |   |     |     | 190 | 98 | 0 | 0 |
| 7 | DMA | 5 | air | 75 | 35 | 96 | 5 | 0 |
|   |     |   |     |     | 100 | 86 | 14 | 0 |
|   |     |   |     |     | 190 | 74 | 23 | 0 |
| 8 | dioxane | 5 | air | 75 | 35 | 95 | 5 | 0 |
|   |     |   |     |     | 100 | 89 | 9 | 0 |
|   |     |   |     |     | 190 | 88 | 12 | 0 |
| 9 | DMF | 5 | air | 75 | 30 | 94 | 6 | 0 |
|   |     |   |     |     | 90 | 90 | 10 | 0 |
|   |     |   |     |     | 170 | 78 | 20 | 0 |
|   |     |   |     |     | 950 | 27 | 73 | 0 |
| 10 | DMC | 5 | air | 75 | 30 | 96 | 4 | 0 |
|   |     |   |     |     | 90 | 88 | 12 | 0 |
|   |     |   |     |     | 170 | 82 | 18 | 1 |
|   |     |   |     |     | 950 | 73 | 26 | 1 |
| 11 | DMA | 5 | air | 140 | 30 | 68 | 32 | 0 |
|   |     |   |     |     | 75 | 42 | 58 | 0 |
|   |     |   |     |     | 230 | 4 | 96 | 0 |
|   |     |   |     |     | 450 | 0 | 100 | 0 |
| 12 | DMA | 0 | air | 140 | 30 | 100 | 0 | 0 |
|   |     |   |     |     | 75 | 99 | 1 | 0 |
|   |     |   |     |     | 230 | 93 | 4 | 0 |
|   |     |   |     |     | 450 | 90 | 6 | 0 |

14-Hydroxymorphinone 3,14-diacetate dissolved slowly in the aprotic polar solvents DMF and DMA. In some experiments, black Pd(0) formed before the starting material was completely dissolved. Batch reactions with 5 mol % of Pd(OAc)$_2$ in either DMF or DMA gave similar results (See Table 9) while reactions in other solvents, such as dioxane, acetonitrile or i-PrOH were significantly slower (See Table 10). The starting material was not soluble in i-PrOH.

The N-demethylation reaction of 14-hydroxymorphinone 3,14-diacetate required considerably longer reaction times than the corresponding reactions with the saturated counterpart oxymorphone 3,14-diacetate. For example, while the reaction of oxymorphone 3,14-diacetate and air (as oxidant) with 5 mol % of Pd(OAc)$_2$ in DMA required 90 min at 120° C. for a complete N-demethylation, the full N-demethylation of 14-hydroxymorphinone 3,14-diacetate was not obtained even after 6 h at 120° C. Complete conversions were obtained, however, after 90 min at 120° C. when oxygen gas rather than air was used as the oxidant (See Table 9). The reaction was relatively clean and the main side-product formed in significant amounts was the N-formyl compound (See FIG. 6). The N-formyl compound is believed to be formed by a palladium-catalyzed oxidation of the N-methylamine group to the formamide in a competing reaction. The N-formyl compound is not an intermediate in the main reaction path leading to the 14-hydroxy-normorphinone. The N-formyl derivative is formed to a lesser extent when air was used as the oxidant.

Example 5

N-Demethylation of 14-Hydroxymorphinone 3,14-Diacetate Using Palladium and Platinum Catalysts The catalyzed aerobic N-demethylation of hydroxymorphinone 3,14-diacetate was performed using both palladium and platinum catalysts. In some embodiments, the formation of Pd(0) can be required to initiate the aerobic N-demethylation reaction. The reactions were tested using different forms of palladium pre-catalyst to form Pd(0), and Pt(0) catalysts.

Initially, 100 mg of hydroxymorphinone 3,14-diacetate (0.26 mmol), either Pd(OAc)$_2$ (5 mol %) or Pd/C (5 mol %) and 1 mL of DMA were combined. The reaction was run at a reaction temperature of 140° C. The reaction mixtures were stirred in an open vial on a hot-plate. Table 11 lists the conversion data for the N-demethylation of hydroxymorphinone 3,14-diacetate. Reactions with palladium on charcoal under batch conditions gave substantially similar results as reactions with Pd(OAc)$_2$ as homogeneous pre-catalyst, e.g., Pd(OAc)$_2$ or Pd/C. With 5 mol % of either pre-catalyst at 140° C., the hydroxymorphinone 3,14-diacetate was substantially fully consumed after a reaction time of about 4 h. The desired 14-hydroxy-normorphinone was the only product detected in the reaction mixture. Not surprisingly, without a catalyst essentially no reaction was observed (See Table 10).

100 mg of hydroxymorphinone 3,14-diacetate (0.26 mmol), catalyst and 1 mL were combined. The reaction mixtures were stirred in an open vial on a hot plate at 140° C. Reactions with palladium on charcoal (10 wt %) under batch conditions gave comparable results to the reactions with Pd(OAc)$_2$ as homogeneous catalyst. (See Entries 1 and 2, Table 11 and Entry 11, Table 10). The reaction with a wet Pd on charcoal did not substantially proceed. (See Entry 3, Table 11 using Pd/C 5 wt % (dry), Degussa-type, wet (~20 wt % H$_2$O)). The reaction proceeded with Pt/C. (See Entry 4, Table 11). Platinum catalyst, e.g., Pt(0), can be an effective catalyst. An additional intermediate compound (X) was detected. This intermediate in the platinum catalyzed demethylation appears to also be converted to 14-hydroxy-normorphinone.

TABLE 11

N-Demethylation of 14-Hydroxymorphinone 3,14-Diacetate on a Hot-Plate at 140° C.

| entry | reaction time [min] | Pd/C 10 wt % [mol %] | 3 [%] | 4 [%] | 5 [%] |
|---|---|---|---|---|---|
| 1 | 30 | 2.5 | 76 | 24 | 0 |
|  | 85 | 2.5 | 51 | 46 | 1 |
|  | 150 | 2.5 | 29 | 69 | 2 |
|  | 230 | 2.5 | 11 | 87 | 2 |
|  | 450 | 2.5 | 0 | 97 | 2 |
| 2 | 30 | 5 | 68 | 30 | 1 |
|  | 85 | 5 | 42 | 56 | 1 |
|  | 150 | 5 | 18 | 80 | 2 |
|  | 230 | 5 | 3 | 95 | 2 |
|  | 450 | 5 | 0 | 97 | 2 |

| entry | reaction time [min] | Pd/C 5 wt % [mol %] | 3 [%] | 4 [%] | 5 [%] |
|---|---|---|---|---|---|
| 3 | 30 | ~4 | 96 | 4 | 0 |
|  | 85 | ~4 | 89 | 11 | 0 |
|  | 150 | ~4 | n.a. | n.a. | n.a. |
|  | 230 | ~4 | 69 | 31 | 0 |
|  | 450 | ~4 | n.a. | n.a. | n.a. |

| entry | reaction time [min] | Pt/C 5 wt % [mol %] | 3 [%] | 4 [%] | X [%] |
|---|---|---|---|---|---|
| 4 | 30 | 5 | 57 | 38 | 4 |
|  | 85 | 5 | 27 | 65 | 9 |
|  | 150 | 5 | 7 | 85 | 8 |
|  | 230 | 5 | 0 | 97 | 3 |
|  | 450 | 5 | 0 | 97 | 0 |

Example 6

Continuous Flow N-Demethylation of 14-Hydroxymorphinone 3,14-Diacetate

The palladium catalyzed aerobic N-demethylation of 14-hydroxymorphinone 3,14-diacetate was performed in a continuous flow reactor system similar to the system described in Example 3. The 14-hydroxymorphinone 3,14-diacetate and 5 mol % of Pd(OAc)$_2$ were dissolved in the respective solvent and injected into the flow reactor. Either 200, 400 or 800 mg of 14-hydroxymorphinone 3,14-diacetate (0.52 to 1.04 mmol), 2.5 or 5 mol % Pd(OAc)$_2$ and 2 to 4 mL solvent were combined. The mixture was combined with an oxygen gas feed controlled by a mass flow controller (gas flow at normal conditions, i.e. =0° C. and p$_n$=1 atm). Tables 12 and 13 list the conversion data for the N-demethylation of hydroxymorphinone 3,14-diacetate.

It was observed that 14-hydroxymorphinone 3,14-diacetate dissolved slowly in DMA and the mixtures were thereafter heated to about 50° C. to dissolve the components prior to introduction to the continuous flow reactor system. Upon heating, Pd(0) formed and the reaction mixture turned black. All continuous flow reactions were performed with oxygen gas as the oxidant in a 20 mL stainless steel coil with a back pressure of about 10 bar or about 20 bar. Substantially complete conversion of 14-hydroxymorphinone 3,14-diacetate was obtained after reaction times of around 20 min at 140° C. with about 2 equiv of oxygen gas. The best results were obtained in DMA as solvent.

The main side product was the N-formyl derivative (5). The reaction temperature can be increased to 160° C. without affecting the purity of the reaction (See Entry 6, Table 12). Oxygen pressure had no appreciable effect on the reaction rate or reaction selectivity even though the residence time was significantly higher at higher back-pressures (See Entries 4 and 5, Table 12). The amount of oxygen used in the flow experiments also had little effect (See Entries 3, 4 and 7, Table 12). Reducing the amount of Pd(OAc)$_2$ to 2.5 equiv at a temperature of 140° C. decreased the conversion to around 85 to 95%, without reducing the selectivity for the N-demethylation reaction appreciably (Entry 9, Table 12 and Table 13). The product from Entry 8, Table 12 using 800 mg of 14-hydroxymorphinone 3,14-diacetate (5 mol % Pd(OAc)$_2$, 1.7 equiv oxygen gas at 145° C.) was isolated by chromatography on a silica column using CHCl$_3$/MeOH as eluent. This provided 674 mg of the pure product (4) (87% isolated yield) in addition to 106 mg of the N-formyl derivative (5) contaminated with small amounts of DMA.

TABLE 12

N-Demethylation of 14-Hydroxymorphinone 3,14-Diacetate (3) under Continuous Flow Conditions.

| entry | solvent/flow rate [mL/min] | O$_2$ flow rate [mL$_N$/min] | stoich. | Pd(OAc)$_2$ [mol %] | temp [° C.] | p [bar] | RT [min] | 3 [%] | 4 [%] | 5 [%] |
|---|---|---|---|---|---|---|---|---|---|---|
| 1 | DMA/0.5 | 10 | 3.4 | 5 | 100 | 12 | 17 | 87 | 11 | 2 |
| 2 | DMA/0.5 | 10 | 3.4 | 5 | 120 | 10 | 18 | 42 | 54 | 4 |
| 3 | DMA/0.5 | 10 | 3.4 | 5 | 140 | 10 | 18 | 7 | 86 | 6 |
| 4 | DMA/0.5 | 6 | 2.1 | 5 | 140 | 9 | 17 | 2 | 90 | 8 |
| 5 | DMA/0.5 | 6 | 2.1 | 5 | 140 | 23 | 29 | 2 | 89 | 6 |
| 6 | DMA/0.5 | 6 | 2.1 | 5 | 160 | 11 | 22 | 0 | 91 | 8 |
| 7 | DMA/0.5 | 5 | 1.7 | 5 | 140 | 11 | 21 | 1 | 88 | 11 |
| 8 | DMA/0.5 | 6 | 2.1 | 2.5 | 140 | 22 | 30 | 6 | 84 | 8 |

TABLE 13

N-Demethylation of 14-Hydroxymorphinone 3,14-Diacetate 3 under Continuous Flow Conditions.

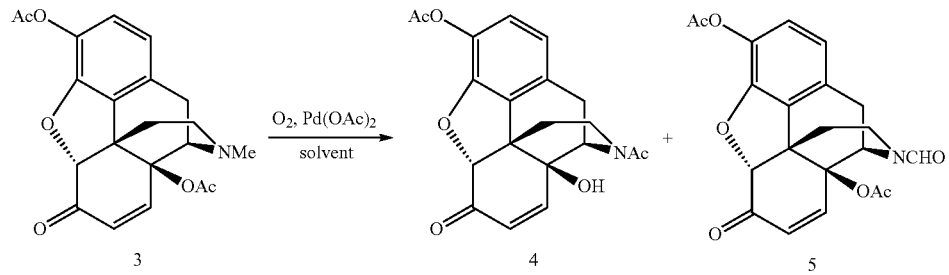

| entry | scale [mg] | solvent/flow rate [mL/min] | O$_2$ flow rate [mL$_N$/min] | stoich. | Pd(OAc)$_2$ [mol %] | temp [° C.] | p [bar] | RT [min] | 3 [%] | 4 [%] | 5 [%] |
|---|---|---|---|---|---|---|---|---|---|---|---|
| 1 | 200 | DMA/0.5 | 10 | 3.4 | 5 | 100 | 12 | 17 | 87 | 11 | 2 |
| 2 | 200 | DMA/0.5 | 10 | 3.4 | 5 | 120 | 10 | 24 | 42 | 54 | 4 |
| 3 | 200 | DMA/0.5 | 10 | 3.4 | 5 | 140 | 10 | 18 | 7 | 86 | 6 |
| 4.1 | 200 | DMA/0.5 | 6 | 2.1 | 5 | 140 | 10 | 18 | 2 | 91 | 7 |
| 4.2 | 200 | DMA/0.5 | 6 | 2.1 | 5 | 140 | 8 | 16 | 0 | 90 | 9 |
| 4.3 | 400 | DMA/0.5 | 6 | 2.1 | 5 | 140 | 8 | 16 | 3 | 88 | 8 |
| 5 | 200 | DMA/0.5 | 6 | 2.1 | 5 | 140 | 23 | 29 | 2 | 89 | 6 |
| 6 | 200 | DMA/0.5 | 6 | 2.1 | 5 | 160 | 11 | 22 | 0 | 91 | 8 |
| 7.1 | 200 | DMA/0.5 | 5 | 1.7 | 5 | 140 | 12 | 25 | 0 | 86 | 14 |
| 7.2 | 200 | DMA/0.5 | 5 | 1.7 | 5 | 140 | 9 | 16 | 3 | 89 | 6 |
| 7.3 | 400 | DMA/0.5 | 5 | 1.7 | 5 | 140 | 9 | 16 | 1 | 89 | 8 |
| 8 | 800 | DMA/0.5 | 5 | 1.7 | 5 | 145 | 9 | 16 | 0 | 90 | 9 |
| 9 | 200 | DMA/0.5 | 6 | 2.1 | 2.5 | 140 | 22 | 30 | 6 | 84 | 8 |
| 10 | 200 | DMA/0.5 | 6 | 2.1 | 2.5 | 140 | 8 | 20 | 17 | 71 | 10 |
| 11 | 200 | DMA/0.5 | 5 | 1.7 | 2.5 | 140 | 8 | 20 | 6 | 83 | 9 |
| 12 | 200 | DMA/0.5 | 5 | 1.7 | 2.5 | 150 | 10 | 18 | 4 | 85 | 10 |
| 13 | 200 | DMF/0.5 | 10 | 3.4 | 5 | 120 | 11 | 23 | 55 | 42 | 2 |
| 14 | 200 | DMF/0.5 | 6 | 2.1 | 5 | 140 | 22 | 31 | 41 | 54 | 0 |
| 15 | 200 | MeCN/0.5 | 6 | 2.1 | 5 | 120 | 9 | 25 | 67 | 27 | 5 |
| 16 | 200 | MeCN/0.5 | 6 | 2.1 | 5 | 140 | 11 |  | 48 | 43 | 5 |
| 17.1 | 200 | Dioxane/0.5 | 6 | 2.1 | 5 | 140 | 12 | 22 | 54 | 39 | 7 |
| 17.2 | 200 | Dioxane/0.5 | 6 | 2.1 | 5 | 140 | 12 | 18 | 48 | 44 | 8 |

Example 7

Formation and Stabilization of Pd(0) in N-Demethylation of 14-Hydroxymorphinone 3,14-Diacetate The palladium catalyzed aerobic N-demethylation of 14-hydroxymorphinone 3,14-diacetate was performed using various pre-heating temperatures and additives to stabilize the Pd(0). 200 mg of 14-hydroxymorphinone 3,14-diacetate (0.52 mmol), 2.5 mol % of Pd(OAc)$_2$ and 2 mL of solvent were combined. The reaction was run at a reaction temperature of 145° C. Table 14 lists the conversion data for the N-demethylation of 14-hydroxymorphinone 3,14-diacetate. For Entry 5, Table 14, the Pd(OAc)$_2$ and acetic acid (stabilizer) were added together and heated in the absence of 14-hydroxymorphinone 3,14-diacetate. The 14-hydroxymorphinone 3,14-diacetate was then added, dissolved and the mixture was injected into the flow reactor.

It was observed that heating of a reaction mixture containing 14-hydroxymorphinone 3,14-diacetate and Pd(OAc)$_2$ for 5 min at 70° C. on a hot plate did not result in the formation of the typical black solution. Upon heating the reaction mixture to 140° C. the catalytically active Pd(0) species was formed and the subsequent continuous flow reaction proceeded as expected (See Entry 2, Table 14). Acetic acid was added to the reaction mixture in either 2, 4 or 10 equivalents. The reaction was improved using AcOH. The addition of about 4 equivalents of AcOH as additive allowed the catalyst loading to be reduced to 2.5 mol % while providing about 95% conversion after a residence time of only about 12 min at 145° C. Furthermore, formation of N-formyl derivative (5) was suppressed in the presence of AcOH (See Entry 6, Table 14).

It is believed that the acetic acid stabilizes the colloidal palladium(0) and prevents its precipitation on the vessel walls. A solution of 60 μL acetic acid and 2.9 mg of Pd(OAc)$_2$ were combined in 2 mL DMA and heated to 140° C. The mixture became black after about 2 min. A second solution of only 2.9 mg of Pd(OAc)$_2$ in 2 mL DMA was prepared and heated to 140° C. The mixture turned black long after 2 min.

14-Hydroxy-normorphinone 3,17-diacetate was converted to noroxymorphone 3,17-diacetate by continuous flow hydrogenation.

Initial hydrogenation reactions were performed using purified 14-hydroxy-normorphinone 3,17-diacetate in a continuous flow hydrogenator (H-Cube Pro™). In this hydrogenator, the reaction mixture was mixed with hydrogen and pumped by a high pressure pump through a catalyst cartridge packed with heterogeneous catalysts on a solid support. Experiments in the hydrogenator using a 5% Pd/C catalyst cartridge resulted in a high back-pressure after the first few runs when DMA was used as the solvent (50 mg 14-hydroxy-normorphinone 3,17-diacetate in 1 mL DMA, 0.5 mL/min flow rate, 40 bar H$_2$ at room temperature). A 5% Pd/Al$_2$O$_3$ catalyst cartridge was tested and full conversion of 14-hydroxy-normorphinone 3,17-diacetate to noroxymorphone 3,17-diacetate was obtained with 40 bar H$_2$ at room temperature (0.5 mL/min flow rate). At pressures below 40 bar lower conversions were observed.

Figure 7:
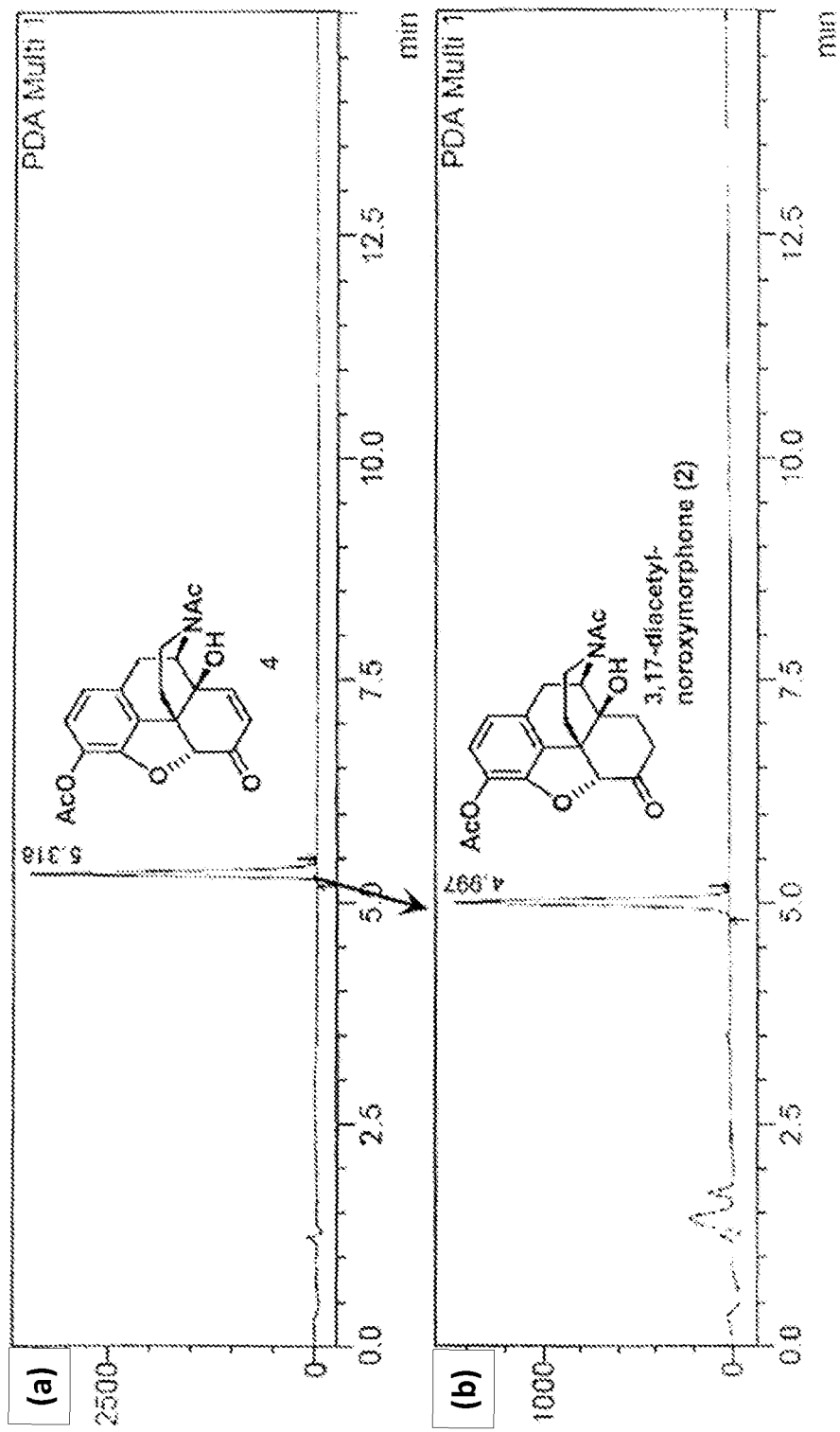
FIG. 7 shows exemplary HPLC-UV chromatograms of the hydrogenation of the 14-hydroxy-normorphinone 3,17-diacetate in a hydrogenator; (a): HPLC trace of starting material, and (b): HPLC trace of product.

FIG. 7 shows the hydrogenation of the purified 14-hydroxy-normorphinone 3,17-diacetate in the hydrogenator. FIG. 7 (a) shows a HPLC-UV chromatogram of the starting material solution having 50 mg of 14-hydroxy-normorphinone 3,17-diacetate in 1 mL DMA. The sample was passed through the hydrogenator having a 5% Pd/Al$_2$O$_3$ catalyst cartridge at 40 bar H$_2$ and 0.5 mL/min flow rate and at room temperature. FIG. 7 (b) shows a HPLC-UV chromatogram of the crude reaction mixture after hydrogenation.

Hydrogenation reactions were performed with the crude product derived from the continuous flow N-demethylation of 14-hydroxymorphinone 3,14-diacetate on a 4.0 g scale. The crude mixture, dissolved in 80 mL of DMA, was pumped through the hydrogenator under the same conditions as described above (i.e., 5% Pd/Al$_2$O$_3$, 40 bar H$_2$, 0.5 mL/min flow rate, room temperature). The mixture passed through the catalyst cartridge and exited the system as a brownish solution. It is believed that a portion of the Pd metal dissolved in the crude reaction mixture and was absorbed on the catalyst cartridge. Despite this, the 14-hydroxy-normorphinone 3,17-diacetate was substantially reduced in this reaction in good yield.

TABLE 14

N-Demethylation of 14-Hydroxymorphinone 3,14-Diacetate under Continuous Flow Conditions.

| entry | pre-heating T/t [° C.]/[min] | color | AcOH [equiv] | flow rate liquid/gas [mL/min] | p [bar] | RT [min] | 3 [%] | 4 [%] | 5 [%] |
|---|---|---|---|---|---|---|---|---|---|
| 1 | 70/5 | orange | 0 | 0.5/5 | 16 | 26 | 77 | 17 | 1 |
| 2 | 140/2 | black | 0 | 0.5/5 | 18 | 28 | 19 | 70 | 7 |
| 3 | 140/2 | black | 0 | 1/10 | 14 | 12 | 34 | 62 | 4 |
| 4 | 140/2 | black | 2 | 1/10 | 17 | 12 | 11 | 87 | 2 |
| 5 | 140/2 | black | 2 | 1/10 | 17 | 12 | 11 | 87 | 2 |
| 6 | 140/2 | black | 4 | 1/10 | 10 | 12 | 5 | 93 | <1 |
| 7 | 140/2 | orange | 10 | 1/10 | 14 | 13 | 53 | 47 | 0 |

Example 8

Continuous Flow Hydrogenation of the 14-Hydroxy-Normorphinone 3,17-Diacetate 14-Hydroxy-normorphinone 3,17-diacetate (4) is the desired product of the palladium catalyzed aerobic N-demethylation of 14-hydroxymorphinone 3,14-diacetate. The

Example 9

Continuous Flow N-Demethylation of Oxymorphone- and/or 14-Hydroxymorphinone-3,14-Diacetate Using Pd(0) and Molecular Oxygen A continuous flow N-demethylation of oxymorphone- and/or 14-hydroxymorphinone-3,14-diacetate with molecular oxygen as oxidant was developed. The reaction was performed with palladium acetate as the catalyst-precursor. Palladium acetate was reduced in-situ to a highly active catalytic palladium(0) species by heating the reaction mixture on a hot plate prior to the flow reaction. Acetic acid was added to stabilize the colloidal palladium(0) particles and increase the efficiency of the subsequent flow reaction.

Continuous flow reactors were found to be ideal systems for these gas-liquid reactions. The oxygen gas was easily and accurately dosed into the liquid feed using mass-flow controllers. High pressure operation increased the amount of oxygen gas dissolved in the liquid feed and the small internal dimension of the stainless steel tube reactor enhanced mass and heat transfer. Complete conversion of 14-hydroxymorphinone-3,14-diacetate was obtained after a residence time of about 20 min at 145° C. with 5 mol % Pd(OAc)$_2$ as catalyst precursor. The reaction was performed on a 100 mg scale up to a 4.0 g scale of starting material and a laboratory scale flow reactor. Subsequent hydrogenation of the noroxymorphone 3,17-diacetate was performed with good selectivity. An industrial process for the production of noroxymorphone on a kilogram scale can be developed based on the present disclosure including continuous flow N-demethylation in a tube reactor, hydrogenation in a packed bed reactor and subsequent hydrolysis.

The continuous flow reactor system included an HPLC pump for pumping the liquid mixture (Uniqsis Pump Module). (See FIG. 4). The pump was connected to a T-mixer (PEEK) via Teflon tubings (1/16" o.d., 0.8 mm i.d.). Oxygen gas from a gas cylinder (purity 5.0) was introduced to the liquid mixture in the T-mixer. The oxygen gas flow was controlled by a mass flow controller (ThalesNano Gas Module). The T-mixer was connected to a 20 mL stainless steel coil (1/16" o.d., 1 mm i.d.) via a 400 µL PFA tubing (1/16" o.d., 0.8 mm i.d.). The PFA tubing allowed visually observation of the flow profile. The 20 mL stainless steel coil was heated in a GC-oven. The reaction mixture exited the system through a short cooling loop (about 400 µL stainless steel in a water bath, 1/16" o.d., 1 mm i.d.) and a back-pressure regulator (either Swagelok (KCB1H0A2A5P60000) or a static BPR from Upchurch Scientific). A pressure sensor, to determine the system pressure, was integrated in the T-mixer (PS2 in FIG. 4) and a second pressure sensor was integrated directly after the pump (PS1 in FIG. 4).

The reaction was performed using 800 mg of 14-hydroxymorphinone 3,14-diacetate (2.1 mmol) and 23.5 mg Pd(OAc)$_2$ (5.0 mol %) dissolved in 8 mL DMA. The 14-hydroxymorphinone 3,14-diacetate dissolved slowly and the mixture was therefore stirred for about 5 min at 70° C. on a hot plate. During this time, the mixture became very dark due to the formation of finely dispersed Pd(0). The mixture was then stirred during the whole flow experiment. DMA was pumped through the flow system at a flow rate of 0.5 mL/min and oxygen gas was introduced into the reactor with a flow rate of 5 mL/min. The temperature of the GC-oven was set to 145° C. When the system was stable, the liquid feed was switched from pure solvent to the liquid mixture solution. About 23 min after the liquid feed was switched from pure solvent to the liquid mixture solution, the product solution left the system. The reaction mixture was collected and concentrated in vacuum and extracted with chloroform/water. Flash chromatography with CHCl$_3$/MeOH as eluent provided 674 mg of 14-hydroxy-normorphinone 3,17-diacetate as a mixture of two amide rotamers (87% isolated yield) in addition to 106 mg of the N-formyl derivative (5) contaminated with small amounts of DMA.

The reaction mixture components were tested using NMR and analytic HPLC-UV chromatography. $^1$H-NMR spectra were recorded on a Bruker 300 MHz instrument. $^{13}$C-NMR spectra were recorded on the same instrument at 75 MHz. Chemical shifts (δ) are expressed in ppm downfield from TMS as internal standard. The letters s, d, t, q and m are used to indicate singlet, doublet, triplet, quadruplet and multiplet. Analytical HPLC-UV (Shimadzu LC20) analysis was carried out on a C18 reversed-phase (RP) analytical column (150×4.6 mm, particle size 5 µm) at 37° C. using a mobile phase A (water/acetonitrile 90:10 (v/v)+0.1% TFA) and B (MeCN+0.1% TFA) at a flow rate of 1.5 mL/min (the following gradient was applied: linear increase from solution 5% B to 80% B in 15 min). Low-resolution mass spectra were obtained on a Shimadzu LCMS-QP2020 instrument using electrospray ionization (ESI) in positive or negative mode.

14-Hydroxy-normorphinone 3,17-diacetate (4) (4:1 mixture of two amide rotamers): colorless solid, m.p. 258° C. (decomp). Major isomer: $^1$H NMR (300 MHz, CDCl$_3$) δ 6.95-6.83 (m, 2H), 6.70 (d, J=8.2 Hz, 1H), 6.15 (d, J=10.1 Hz, 1H), 5.19 (d, J=4.8 Hz, 1H), 4.99 (s, 1H), 4.81 (s, 1H), 3.70 (dd, J=13.9, 4.8 Hz, 1H), 3.17 (td, J=13.4, 3.9 Hz, 1H), 3.11-2.93 (m, 1H), 2.64 (td, J=12.7, 5.3 Hz, 1H), 2.28 (s, 3H), 2.14 (s, 3H), 2.07 (m, 1H), 1.73 (dd, J=12.6, 3.2 Hz, 1H). $^{13}$C NMR (75 MHz, CDCl$_3$) δ 193.3, 171.2, 168.3, 148.7, 147.5, 133.5, 132.6, 130.6, 129.7, 123.4, 120.0, 87.3, 67.7, 52.5, 47.3, 40.0, 31.6, 27.7, 22.0, 20.7. m/z MS (pos. ESI): m/z=370 (M+H$^+$).

14-Hydroxy-normorphinone 3, 14-diacetate 17-formate (5) (1:1 mixture of two amide rotamers; contaminated with DMA): $^1$H NMR (300 MHz, CDCl$_3$) δ 8.09 (s, 1H), 8.04 (s, 1H), 6.89-6.79 (m, 4H), 6.65 (d, J=8.2 Hz, 2H), 6.21 (d, J=7.2 Hz, 1H), 6.18 (d, J=7.2 Hz, 1H), 5.47 (d, J=4.8 Hz, 1H), 4.77 (s, 1H), 4.75 (s, 1H), 4.62 (d, J=3.6 Hz, 1H), 4.35 (dd, J=14.0, 5.3 Hz, 1H), 3.46 (dd, J=13.9, 5.2 Hz, 1H), 3.25-3.13 (m, 1H), 3.11-2.96 (m, 4H), 2.74-2.62 (m, 1H), 2.28-2.07 (m, 5H), 2.01 (s, 3H), 2.00 (s, 3H), 1.97 (s, 3H), 1.80 (td, J=12.8, 3.9 Hz, 2H). $^{13}$C NMR (75 MHz, CDCl$_3$) δ 191.8, 191.6, 170.0, 169.8, 168.1, 168.1, 161.7, 161.4, 147.9, 147.9, 141.7, 141.4, 136.2, 135.8, 132.9, 132.9, 129.5, 129.3, 129.2, 128.9, 124.2, 124.0, 120.1, 120.0, 87.6, 87.5, 75.8, 75.1, 55.2, 48.8, 48.3, 48.2, 39.7, 33.4, 32.30, 31.08, 28.4, 27.6, 21.4, 21.4, 20.6, 20.6. m/z MS (pos. ESI): m/z=398 (M+H$^+$).

The product of the continuous flow N-demethylation of 14-hydroxymorphinone-3,14-diacetate subsequently hydrogenated in a continuous flow hydrogenation process. The concentrated crude material from a continuous flow N-demethylation on a 4 g scale was re-dissolved in 80 mL DMA and subsequently pumped through the hydrogenator. The hydrogenator conditions included: 5% Pd/Al$_2$O$_3$ catalyst cartridge; 0.5 mL/min flow rate; 25° C. reaction temperature; 40 bar; full H$_2$ mode. The mixture passed through the hydrogenator and exited the system as a yellowish to brownish solution. 1.5 min after the feed was switched from solvent (DMA) to the reaction mixture, the product was collected (first product appeared after about 5.5 min). The N-acetyl compound (4) was essentially completely reduced to the 7,8-dihydro product (2) under these conditions. However, only about 75% of the N-formyl compound (5) was hydrogenated to the corresponding dihydro product in the first fraction. This fraction was again pumped through the hydrogenator under the same conditions. All fractions were combined and the combined sample was concentrated in vacuum to provide 6.3 g of a dark, viscous oil as the crude product and analyzed.

Noroxymorphone 3,17-diacetate (2) (4:1 mixture of two amide rotamers): Major isomer: $^1$H NMR (300 MHz, CDCl$_3$) δ 6.87 (d, J=8.2 Hz, 1H), 6.69 (d, J=8.2 Hz, 1H), 5.06 (d, J=5.8 Hz, 1H), 4.70 (s, 1H), 4.29 (s, 1H), 3.64 (dd, J=13.9, 4.9 Hz, 1H), 3.16-3.07 (m, 3H), 2.89 (d, J=18.8 Hz, 1H), 2.62 (td, J=12.8, 5.2 Hz, 1H), 2.33 (s, 3H), 2.30 (m, 1H), 2.17 (s, 3H), 2.00 (m, 1H), 1.70 (ddd, J=13.9, 8.7, 3.5 Hz, 1H), 1.59 (dd, J=12.6, 3.1 Hz, 1H). $^{13}$C NMR (75 MHz, CDCl$_3$) δ 207.2, 171.0, 168.4, 147.9, 132.8, 129.6, 129.3, 123.4, 119.9, 90.2, 70.4, 53.3, 50.4, 39.9, 35.7, 31.8, 31.6, 28.8, 22.1, 20.8. m/z MS (pos. ESI): m/z=372 (M+H$^+$).

Example 10

Continuous Flow N-Demethylation of 14-Hydroxymorphinone-3,14-Diacetate using Pd(0) Coated Stainless Steel Coil Palladium can deposit on the stainless steel coil reactor in the form of a thin film of metallic palladium. The extent and utility of the deposited palladium was determined. Two reaction mixtures were prepared each having 200 mg of 14-hydroxymorphinone-3,14-diacetate, 5.9 mg Pd(OAc)$_2$ (5 mol %) and 2 mL of DMA. One of the reaction mixtures was pumped through the continuous flow reactor system under the following reaction conditions: 20 mL stainless steel coil, 140° C., 0.5 mL/min flow rate, 5 mL/min oxygen gas. The other reaction mixture was not pumped through the reactor system. Both reaction mixtures (the processed and the un-processed mixture) were digested with HNO$_3$/HCl and analyzed by ICP-MS (each sample was digested and analyzed in triplicate). Table 15 lists the amount of palladium determined.

The expected total amount of palladium in each sample was about 2.80 mg. The total amount of palladium in the collected reaction mixture was significantly less. About 60% of the palladium is lost in the flow reactor system.

TABLE 15

ICP-MS Analysis of Reaction Mixtures Before and After a Flow Reaction.

| entry | mixture | Pd detected in Sample [μg/mL] | sample amount [mg] | total Pd in Sample [mg] |
|---|---|---|---|---|
| 1 | Before reaction | 1320 ± 10 | 2094.8 | 2.95 ± 0.02 |
| 2 | After reaction | 154 ± 5 | 7258.3 | 1.19 ± 0.04 |

Additional N-demethylation reactions in the same stainless steel coil were performed using 200 mg of 14-hydroxymorphinone-3,14-diacetate in 2 mL DMA under the conditions stated above, and without palladium catalyst in the mixture. Demethylation reactions in the stainless steel coil under standard flow conditions, but without Pd in the mixture, gave conversions of 57% (See Entry 1, Table 16). After the first reaction the system was washed with DMA at 145° C. for over 1 hour. A subsequent reaction using of 14-hydroxymorphinone-3,14-diacetate in 2 mL DMA without palladium was performed and produced a conversion of about 78% (See Entry 2, Table 16). Two further reactions were performed under these conditions. The reactor was again washed with DMA at 145° C. for over 1 hour between each reaction. The "palladated" coil did not lose any activity during these four reactions. More of the formamide side-product (5) was formed in these reactions compared to reactions under standard reaction conditions (normally it is ~10% at a full conversion of hydroxymorphinone (3)).

TABLE 16

"Palladium free" N-Demethylation of 14-Hydroxymorphinone-3,14-Diacetate under Continuous Flow Conditions.

| entry | RT [min] | 3 [%] | 4 [%] | 5 [%] |
|---|---|---|---|---|
| 1$^b$ | 25 | 43 | 44 | 8 |
| 2 | 24 | 22 | 65 | 13 |
| 3 | 25 | 12 | 68 | 18 |
| 4 | 25 | 12 | 67 | 19 |

All publications, patents, and patent applications are herein incorporated by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While this disclosure has been particularly shown and described with reference to example embodiments thereof, it will be understood by those skilled in the art that various changes in form and details may be made therein without departing from the scope of the invention encompassed by the appended claims.

We claim:

1. A process for the N-demethylation of a compound containing a tertiary N-methylamine, wherein the compound is a compound of formula I:

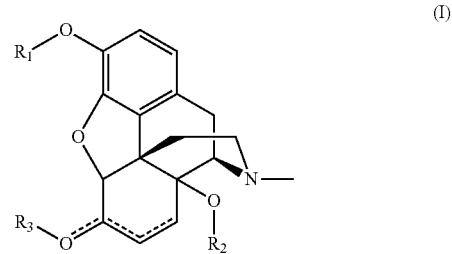

(I)

wherein
each ==== independently represents a single or double bond, provided that two double bonds are not adjacent to each other;
R$_1$ and R$_3$ are each independently selected from the group consisting of C(O)R$_4$, C$_{1-10}$ alkyl, C$_{6-10}$ aryl, C$_{3-10}$ cycloalkyl, C$_{1-10}$ alkylene-C$_{6-10}$ aryl, C$_{1-10}$ alkylene-C$_{3-10}$ cycloalkyl and PG;
R$_2$ is selected from the group consisting of C(O)R$_4$, S(O)R$_4$, SO$_2$R$_4$, P(O)R$_4$R$_5$, P(O)(OR$_4$)R$_5$, and P(O)(OR$_4$)(OR$_5$), and
R$_4$ and R$_5$ are each independently selected from C$_{3-10}$ cycloalkyl, C$_{3-10}$ heterocycloalkyl, C$_{3-10}$ cycloalkenyl, C$_{1-10}$ alkyl, C$_{2-10}$ alkenyl, C$_{6-10}$ aryl and C$_{5-10}$ heteroaryl, each of the latter groups being unsubstituted or substituted with one or more substituents independently selected from C$_{1-4}$ alkyl, OC$_{1-4}$ alkyl, halo, CN, NO$_2$, C$_{6-10}$ aryl and OC$_{6-10}$ aryl, comprising the steps of:
(i) providing a liquid mixture containing the compound, a metal catalyst and a solvent; and (ii) contacting the liquid mixture with a gaseous oxidant or an organic peroxide oxidant to form a reaction mixture whereby the compound and oxidant contained in the reaction mixture react to form a N-demethylated form of the compound in a continuous flow system.

2. The process of claim 1, wherein the metal catalyst comprises palladium, platinum, ruthenium, iron, tungsten, vanadium, iridium, copper, gold, silver or combinations thereof.

3. The process of claim 1, wherein the metal catalyst comprises palladium or platinum.

4. The process of claim 1, wherein the metal catalyst comprises palladium.

5. The process of claim 1, wherein the metal catalyst is selected from the group consisting of $Pd(OAc)_2$, $PdCl_2$, $PdCl_2(PPh_3)_4$, $PdBr_2$, $Pd(acac)_2$, $Pd2(dba)_3$, $Pd(dba)_2$, $Pd(PPh_3)_4$, $PtCl_2$, $K_2PtCl_4$, Ru/C, $RuCl_3H_2O$, $RuCl_2(PPh_3)_3$, $RuO_2$, a tetrapropylammonium perruthenates, $FeCl_2$, $FeSO_4$, $Fe_2(CO)_9$, $Na_2WO_4$, $VO(acac)_2$, $Pd(OAc)_2$, $Pd(acac)_2$, Pd black, a palladium-perovskite, and combinations thereof.

6. The process of claim 1, wherein the metal catalyst is present in the liquid mixture in about 0.01 to about 0.05 equivalents of the compound containing a tertiary N-methylamine.

7. The process of claim 1, further comprising the step of hydrogenating the N-demethylated form of the compound.

8. The process of claim 1, wherein the compound is selected from the group consisting of oxymorphone-3,14-diacetate and 14-hydroxymorphinone-3,14-diacetate.

9. The process of claim 1, wherein the oxidant is oxygen gas.

10. The process of claim 1, wherein the organic peroxide oxidant is t-butyl hydroperoxide.

11. The process of claim 1, wherein the liquid mixture further comprises acetic acid.

12. The process of claim 11, wherein the acetic acid is present in the liquid mixture in about 1 to about 4 equivalents of the compound containing a tertiary N-methylamine.

13. The process of claim 1, wherein the yield of the N-demethylated form of the compound is greater than 80%.

14. The process of claim 1, wherein the steps in the continuous flow system are carried out at a pressure between 1 and 100 bar.

15. The process of claim 1, wherein the steps in the continuous flow system are carried out at a temperature between 70° C. and 200° C.

16. The process of claim 1, wherein the solvent is selected from the group consisting of dimethylformamide, dimethylsulfoxide, N-methylpyrrolidone, and dimethylacetamide.

17. The process of claim 1, wherein the solvent comprises dimethylacetamide.

18. The process of claim 1, wherein the steps are performed in a continuous manner.

19. The process of claim 1, wherein the process is performed in less than about 60 minutes.

20. The process of claim 1, further comprising isolating the N-demethylated form of the compound.

21. The process of claim 1, wherein the metal catalyst is a Pd(0) catalyst, the method further comprising the steps of:
(iii) before step (i), preparing a liquid mixture of the compound and a Pd(II) compound, such that the Pd(II) compound is converted to a Pd(0) catalyst.

22. The process of claim 21, wherein step (iii) is carried out at a temperature between about 70° C. and about 200° C.

23. The process of claim 21, wherein step (iii) is performed in less than about 30 minutes.

24. The process of claim 21, wherein the Pd(II) compound is palladium acetate.

* * * * *